(12) United States Patent
Srinivasa Naidu et al.

(10) Patent No.: US 11,950,959 B2
(45) Date of Patent: Apr. 9, 2024

(54) ULTRASOUND SYSTEM WITH AUTOMATED DYNAMIC SETTING OF IMAGING PARAMETERS BASED ON ORGAN DETECTION

(71) Applicant: KONINKLIJKE PHILIPS N.V., Eindhoven (NL)

(72) Inventors: Raghavendra Srinivasa Naidu, Auburndale, MA (US); Claudia Errico, Cambridge, MA (US); Hua Xie, Cambridge, MA (US); Haibo Wang, Melrose, MA (US); Scott William Dianis, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 382 days.

(21) Appl. No.: 17/262,435

(22) PCT Filed: Jul. 19, 2019

(86) PCT No.: PCT/EP2019/069491
§ 371 (c)(1),
(2) Date: Jan. 22, 2021

(87) PCT Pub. No.: WO2020/020770
PCT Pub. Date: Jan. 30, 2020

(65) Prior Publication Data
US 2021/0353260 A1   Nov. 18, 2021

Related U.S. Application Data

(60) Provisional application No. 62/703,491, filed on Jul. 26, 2018.

(51) Int. Cl.
*A61B 8/08* (2006.01)
*A61B 8/00* (2006.01)
*G06N 3/04* (2023.01)

(52) U.S. Cl.
CPC .......... *A61B 8/5207* (2013.01); *A61B 8/5292* (2013.01); *A61B 8/54* (2013.01); *A61B 8/585* (2013.01); *G06N 3/04* (2013.01)

(58) Field of Classification Search
None
See application file for complete search history.

(56) References Cited

U.S. PATENT DOCUMENTS 6,443,896 B1  9/2002  Detmer
6,530,885 B1  3/2003  Entrekin et al.
(Continued)

OTHER PUBLICATIONS

PCT/EP2019/069491 OSR & WO, Nov. 8, 2019, 17 Page Document.
Szegedy et al: "Going Deeper With Convolutions"; Computer Vision Foundation, 2015, pp. 1-9.

*Primary Examiner* — Joel Lamprecht
*Assistant Examiner* — Nyrobi Celestine

(57) ABSTRACT

The present disclosure describes ultrasound imaging systems and methods for ultrasonically inspecting biological tissue. An ultrasound imaging system according to the present disclosure may be configured to automatically apply tissue-specific imaging parameter settings (312, 314) based upon the automatic identification of the type of tissue being scanned. Tissue type identification (315) may be performed automatically for the images in the live image stream (304) and thus adjustments to the imaging settings may be applied automatically by using a neural network (320) and thus dynamically during the exam obviating the need for the sonographer to manually switch presets or adjust the imaging settings when moving to different portion of the anatomy.

23 Claims, 15 Drawing Sheets

(56) References Cited

U.S. PATENT DOCUMENTS

| | | | |
|---|---|---|---|
| 2009/0264757 A1* | 10/2009 | Yang | G01S 7/52082 600/443 |
| 2012/0157843 A1* | 6/2012 | Lavin | G01S 7/52098 600/443 |
| 2013/0253317 A1 | 9/2013 | Gauthier | |
| 2016/0317127 A1 | 11/2016 | Dos Santos Mendonca et al. | |
| 2018/0075597 A1* | 3/2018 | Zhou | A61B 6/037 |
| 2018/0144466 A1 | 5/2018 | Hsieh et al. | |
| 2018/0160981 A1 | 6/2018 | Tsymbalenko et al. | |
| 2019/0269384 A1* | 9/2019 | Lundberg | G16H 50/20 |
| 2019/0350564 A1* | 11/2019 | Gajdos | G09B 23/286 |
| 2021/0000449 A1* | 1/2021 | Deo | G06N 3/08 |

\* cited by examiner

```
<Event TimeStamp="2017-08-18T08:11:37" TimeFraction="700613" Index="0">
  <EventOriginatorInfo/>
  <EventInfo InfoCategory="UserAction" LogCategory="Utilization" EventCategory="Information" Description="IMAGING_START" >
  <AdditionalInfo  >
    <Xdcr>X7_2T</Xdcr>
    <ImagingMode>Echo2D</ImagingMode>
  </AdditionalInfo>
  </EventInfo>
</Event>

<Event TimeStamp="2017-08-18T08:11:38" TimeFraction="395653" Index="0">
  <EventOriginatorInfo/>
  <EventInfo InfoCategory="UserAction" LogCategory="Utilization" EventCategory="Information" Description="PRESET_ACTIVATED" >
  <AdditionalInfo  >
    <Preset>Adult echo</Preset>
  </AdditionalInfo>
  </EventInfo>
</Event>
```

```xml
<Event TimeStamp="2017-08-18T08:12:04" TimeFraction="477145" Index="0">
  <EventOriginatorInfo/>
  <EventInfo InfoCategory="UIEvent" LogCategory="Workflow" EventCategory="Information" Description="EVTMGR_CP_DEPTH_CHANGE" >   722-1
    <AdditionalInfo >
      <InputType>UiInput</InputType>
      <ClientId>INTERFACE_ID_APPUI_EVENT_REPLAY</ClientId>
      <MethodName>sendCPEvent</MethodName>
      <MethodId>APPUIMAINSENDCPEVENTMETHOD</MethodId>
      <event>EVTMGR_CP_DEPTH_CHANGE</event>
      <ctrlType>64</ctrlType>
      <value>1</value>   724-1
    </AdditionalInfo>
  </EventInfo>
</Event>
<Event Timestamp="2017-08-18T08:12:08" Timefraction="141354" Index="0">
  <EventOriginatorInfo/>
  <EventInfo InfoCategory="UIEvent" LogCategory="Workflow" EventCategory="Information" DESCRIPTION=EVTMGR_CP_DEPTH_CHANGE">   722-1
    <AdditionalInfo >
      <InputType>UiInput</InputType>
      <ClientId>INTERFACE_ID_APPUI_EVENT_REPLAY</ClientId>
      <MethodName>sendCPAccuEvent</MethodName>
      <MethodId>APPUIMAINSENDCPACCUEVENTMETHOD</MethodId>
      <event>EVTMGR_CP_DEPTH_CHANGE</event>
      <ctrlType>64</ctrlType>
      <value>2</value>
      <count>2</count>   724-2
    </AdditionalInfo>
  </EventInfo>
</Event>
```

Wrong preset

Too flat (compression)

Too smooth (persistence)

Abdominal preset

Right preset

Right contrast setting

No temporal smoothing

Cardiac preset

ULTRASOUND SYSTEM WITH AUTOMATED DYNAMIC SETTING OF IMAGING PARAMETERS BASED ON ORGAN DETECTION

CROSS-REFERENCE TO PRIOR APPLICATIONS

This application is the U.S. National Phase application under 35 U.S.C. § 371 of International Application No. PCT/EP2019/069491, filed on Jul. 19, 2019, which claims the benefit of U.S. Provisional Patent Application No. 62/703,491, filed on Jul. 26, 2018. These applications are hereby incorporated by reference herein.

TECHNICAL FIELD

The present disclosure pertains to ultrasound imaging systems and methods for ultrasonically inspecting biological tissue, and more specifically systems configured to automatically adjust the imaging parameters of the system to tissue specific settings based on organ detection.

BACKGROUND

Ultrasound imaging is commonly used to non-invasively image internal tissue or organs of a patient, e.g., for diagnosing any number of different diseases or the monitoring of the progression or success of treatment thereof. When performing an ultrasound examination, the user (e.g., sonographer or clinician) may need to often adjust imaging parameter settings (e.g., depth, focus, frequency, gain, TGC, imaging mode, etc.) to obtain a quality image.

In a typical system, before initiating any ultrasound examination, the user is asked to choose a preset, which sets one or more imaging parameters of the system to settings that are generally optimized for the specific organ/tissue under investigation. A tissue specific preset (TSP) therefore defines the settings for one or more of the imaging parameters of the system that may be suitable for a specific imaging application. Modern imaging systems provide a user interface for switching between different TSPs. A user selection screen may be presented to the user, e.g., based on transducer application types, for the user to select a TSP that the user thinks is appropriate. Due to presence of wide varieties of TSPs in a typical imaging system, users could accidently select a preset that is not the best fit for a given patient. This may happen for example when the clinician performs, during the same scanning session, examination of multiple organs of a patient which may be better imaged at different settings. Also, in emergency settings users do not generally have the time to pre-select the proper TSP and may end up performing an exam with the wrong parameters, leading to suboptimal ultrasound images and incorrect quantitative measurement. Thus, designers and manufacturers of ultrasound imaging system continue to seek improvements thereto.

SUMMARY

The present disclosure pertains to ultrasound imaging systems and methods for ultrasonically inspecting biological tissue, and more specifically systems configured to automatically adjust the imaging parameters of the system to tissue specific settings based on organ detection.

In accordance with some examples of the present disclosure, an ultrasound system may include a probe configured to transmit ultrasound toward a subject for generating ultrasound images of biological tissue of the subject, and a processor configured to generate and to cause the ultrasound imaging system to display, in real-time, a live stream of ultrasound images of the biological tissue in accordance with a plurality of imaging parameters of the ultrasound system.

The processor may be further configured to receive, in real-time, an ultrasound image from the live stream of ultrasound images, receive an identification of a type of the biological tissue in the ultrasound image, based on the type of the biological tissue and in some cases one or more additional input parameters, generate at least one predicted setting for at least one of the plurality of imaging parameters, and automatically apply the at least one predicted setting to the respective imaging parameter for subsequent live imaging. In some embodiments, the processor may employ a neural network to generate the predicted setting(s). In some embodiments the identification of the biological tissue is performed by the processor, for example using a machine-learning model, such as a properly trained machine-learning organ classification model. In some examples, the system may optionally additionally include memory which stores a plurality of presets each defining one or more settings for at least one of the imaging parameters of the ultrasound imaging system, and the processor may be configured to select one of the plurality of stored presets based on the type of the biological tissue and to automatically apply the selected preset to adjust one or more of the plurality of imaging parameters of the system to settings defined by the selected preset, e.g., prior to or while generating the at least one predicted setting. In some examples, the predicted setting may be generated using, as inputs, the imaging settings defined by the selected preset, e.g., by a machine-learning model properly trained to tailor the preset settings according to patient-specific and/or user-specific preferences.

In some examples, the system may utilize a machine-learning regression model appropriately trained to generate the patient-specific and/or user-specific setting(s), which are also referred to herein as predicted setting(s). In some examples, the regression model may be trained using data extracted from system logs from multiple ultrasound imaging systems. In some examples, the artificial neural network used by the ultrasound system may be configured to output at least one predicted setting responsive to inputs including the type of the biological tissue, user identification information, patient identification information, and a respective setting defined by the selected preset. In some examples, the artificial neural network may include a plurality of layers including a first input layer configured to receive an input of size n+i and an output layer configured to generate an output of size n, and wherein n is equal to a number of the settings defined by the selected preset.

A method of ultrasonically inspecting biological tissue in accordance with some examples may include receiving, in real-time, by a processor of an ultrasound system, an ultrasound image from a live stream of ultrasound images, receiving an identification of a type of the biological tissue in the ultrasound image, selecting one of a plurality of presets stored in a memory of the ultrasound system based on the type of the biological tissue in the ultrasound image, automatically adjusting one or more imaging parameters of the ultrasound system to settings defined by the selected preset, based on the type of the biological tissue, identifying, using an artificial neural network, one or more user-specific settings, patient-specific settings, or a combination thereof for at least one of the one or more of the imaging parameters, and automatically adjusting the at least one imaging parameter in accordance with the one or more user-specific settings, patient-specific settings, or the combination thereof for subsequent live imaging.

Any of the methods described herein, or steps thereof, may be embodied in non-transitory computer-readable medium comprising executable instructions, which when executed may cause a processor of a medical imaging system to perform the method or steps embodied herein.

BRIEF DESCRIPTION OF THE DRAWINGS

FIGS. 7A and 7B show portions of ultrasound system logs which capture settings adjustments made during ultrasound scanning, which may be used to compile training data for a settings prediction model according to the present disclosure.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Figure 10A:
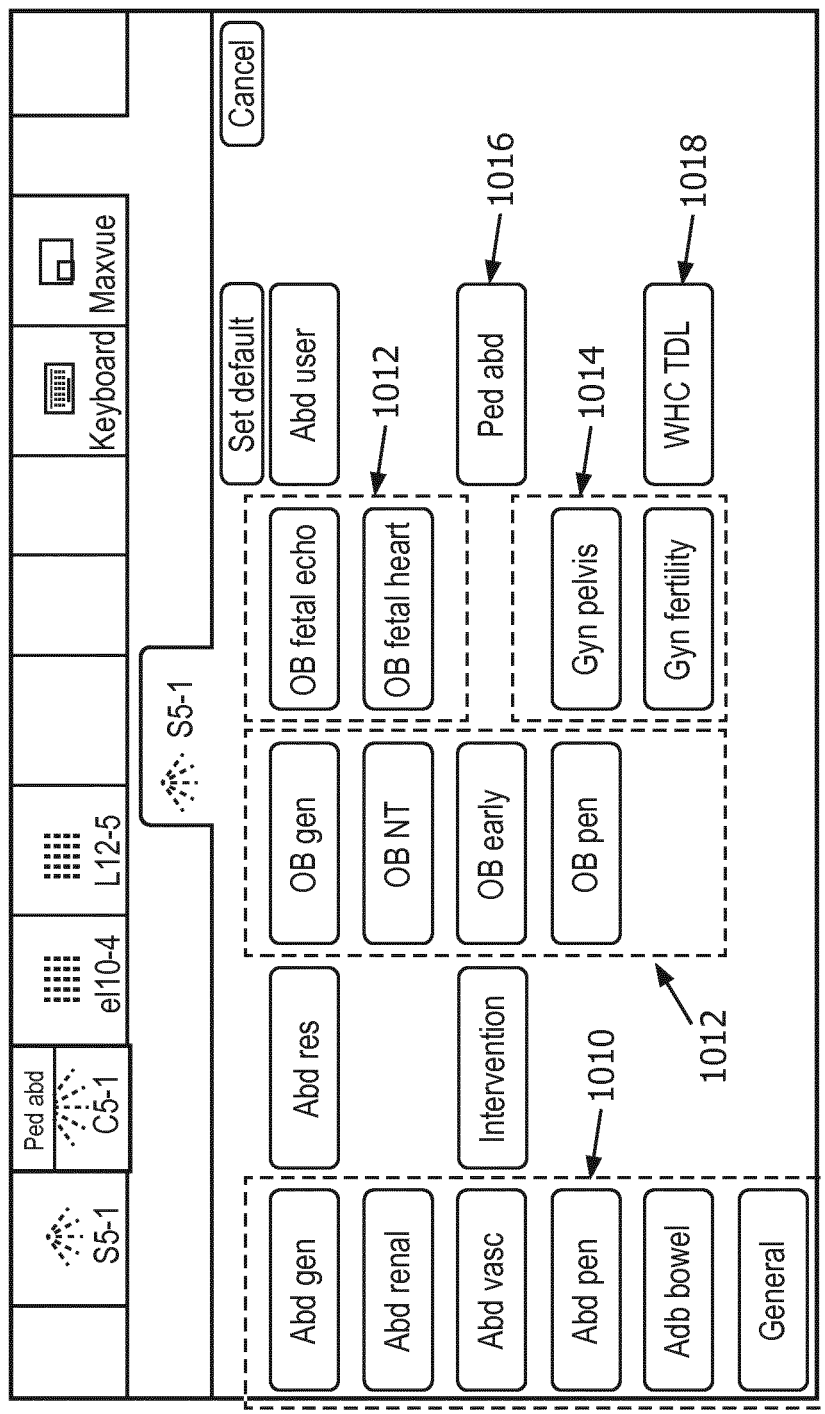
FIGS. 10A, 10B and 10C show screen captures of a graphical user interfaces for manually selecting a preset on an example ultrasound system in accordance with some examples herein.
Figure 10B:
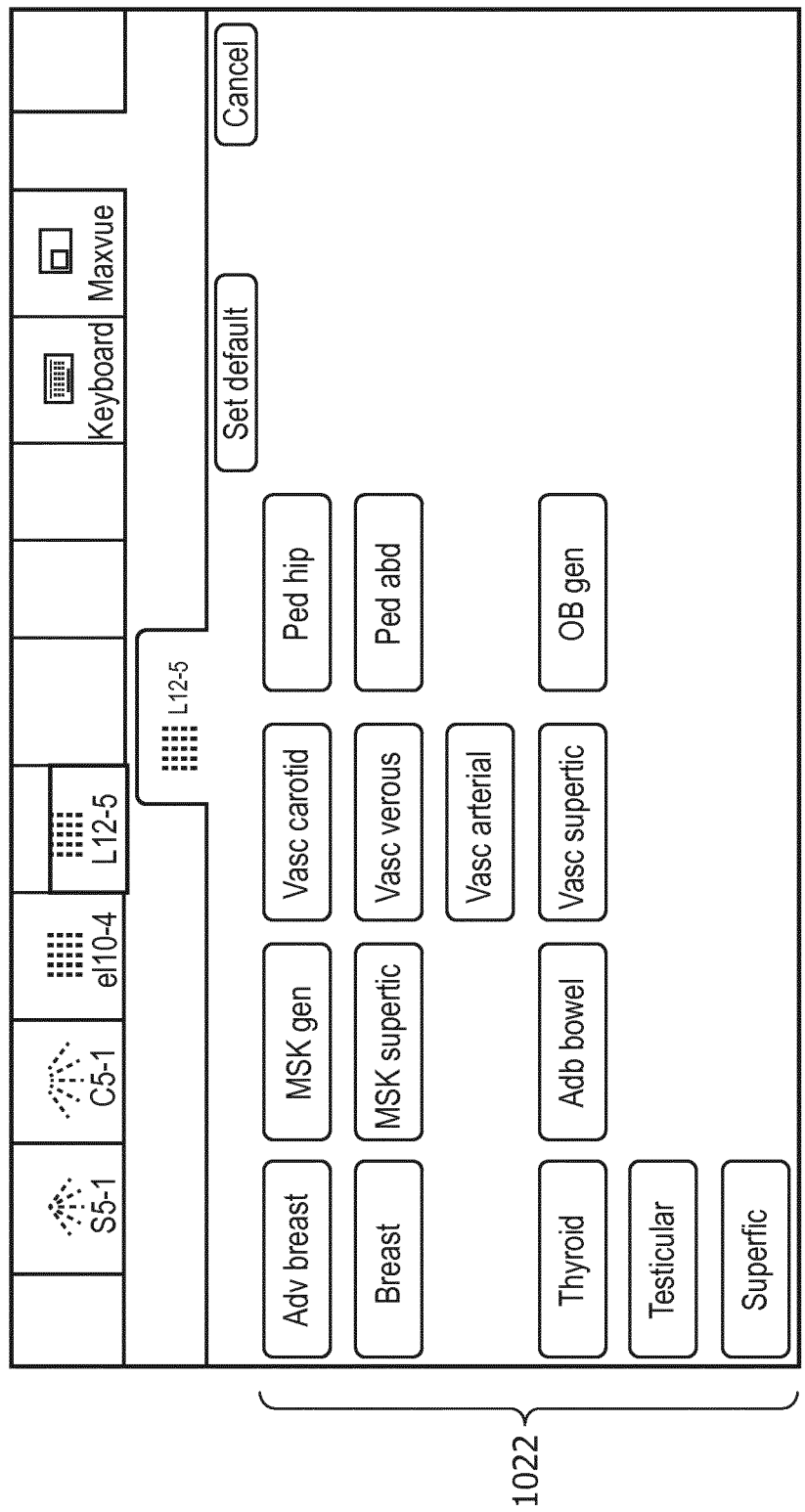
Figure 10C:
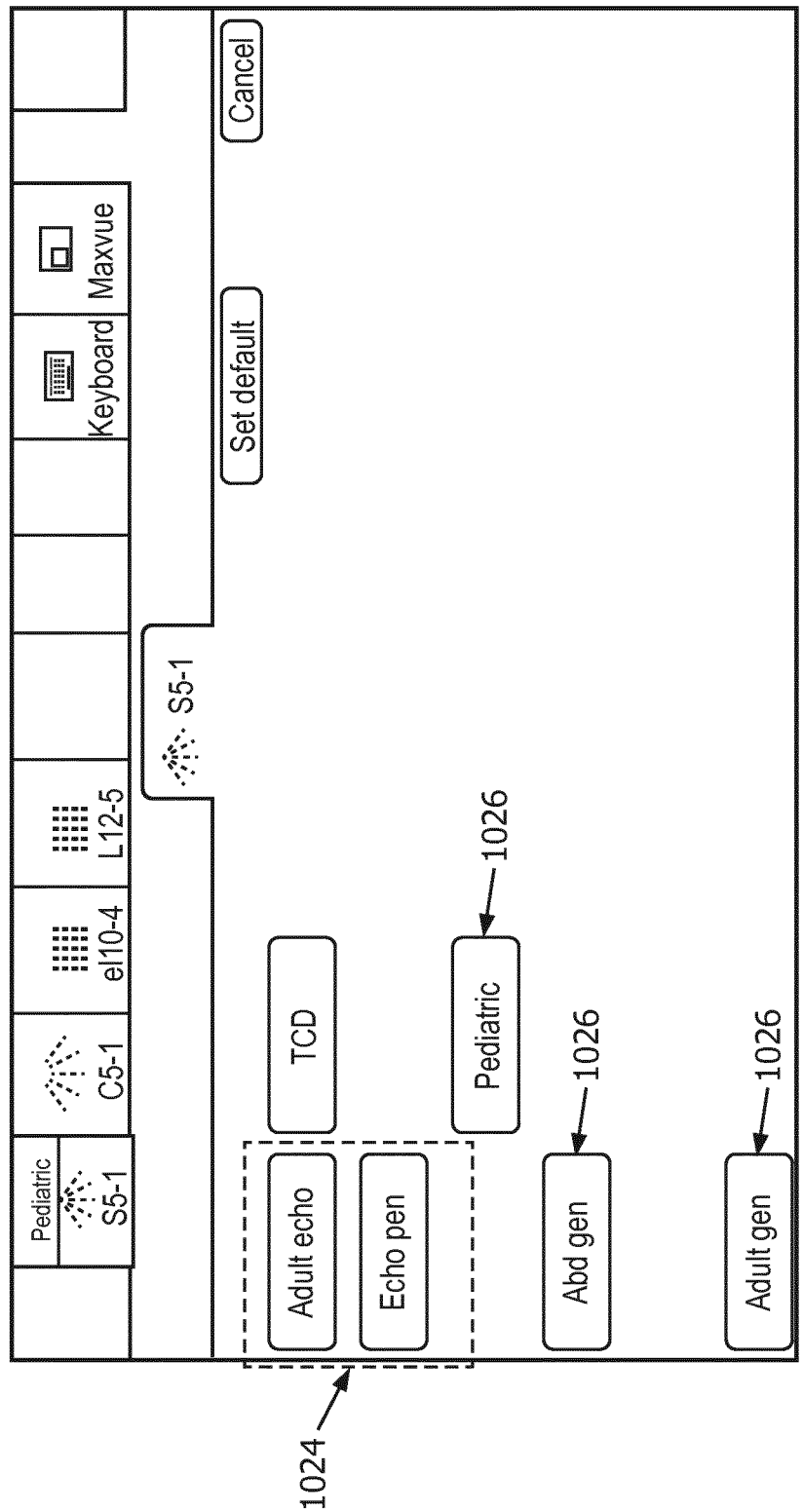

Ultrasound imaging systems include a number of re-configurable imaging parameters, which control, for example, the brightness/contrast on the images (gain), the depth at which the ultrasound beam is focused, the imaging frequency, the time gain compensation (TCG), the users mode (i.e. fundaments frequency imaging, tissue harmonic imaging, and compound imaging), and the flow velocity range for Color-Doppler quantifications. Other imaging parameters may include the focus (or focal zone), line density, persistence, dynamic range for display (or Compression), etc. Different organs and structure of the human body may require very different imaging parameters and the correct choice of imaging parameters has a great impact on the readability and interpretation of the output image for the end user (e.g. radiologists). For example, as shown in FIGS. 10A-C, a number of different presets may be available for a given transducer type on a typical modern ultrasound system (in this example, on the ultrasound imaging system sold by PHILIPS under the brand name EPIQ) for a given imaging application (e.g., abdominal, breast, and cardiac). FIG. 10A shows a user interface for selecting among available presets for abdominal imaging, which is often performed using the PHILIPS C5-1 curvilinear probe. As illustrated, six different presets 1010 are available for abdominal imaging, six presets 1012 for Obstetric imaging, two presets 1014 are available for Gynecological imaging, and one preset 1016 for Pediatric abdominal exams, as well as additional optional presets 1018 (e.g., WHC TDI, intervention, etc.) for other imaging applications. FIG. 10B shows a user interface for selecting among available presets for superficial or breast imaging, which is often performed using the PHILIPS L12-5 linear probe. As illustrated, a number of different presets 1022 are available including Breast, Thyroid, Testicular, Superficial, Musculoskeletal (MSK) General and Superficial, Abdominal bowel, Pediatric Abdominal, Obstetric General, and a variety of presets for Vascular applications (e.g., Carotid, Venous, Arterial, Superficial). FIG. 10C shows a selection interface for presets associated with the PHILIPS S5-1 sector array probe, which can be used for cardiac imaging, and thus may be associated, on this exemplary system, with presets 1024 for echocardiographic applications (e.g., Adult Echo, Echo Pen), as well as presets 1026 for other imaging applications (e.g., Abdominal General, Adult General, Pediatric, etc.).

Figures 11A, 11B:
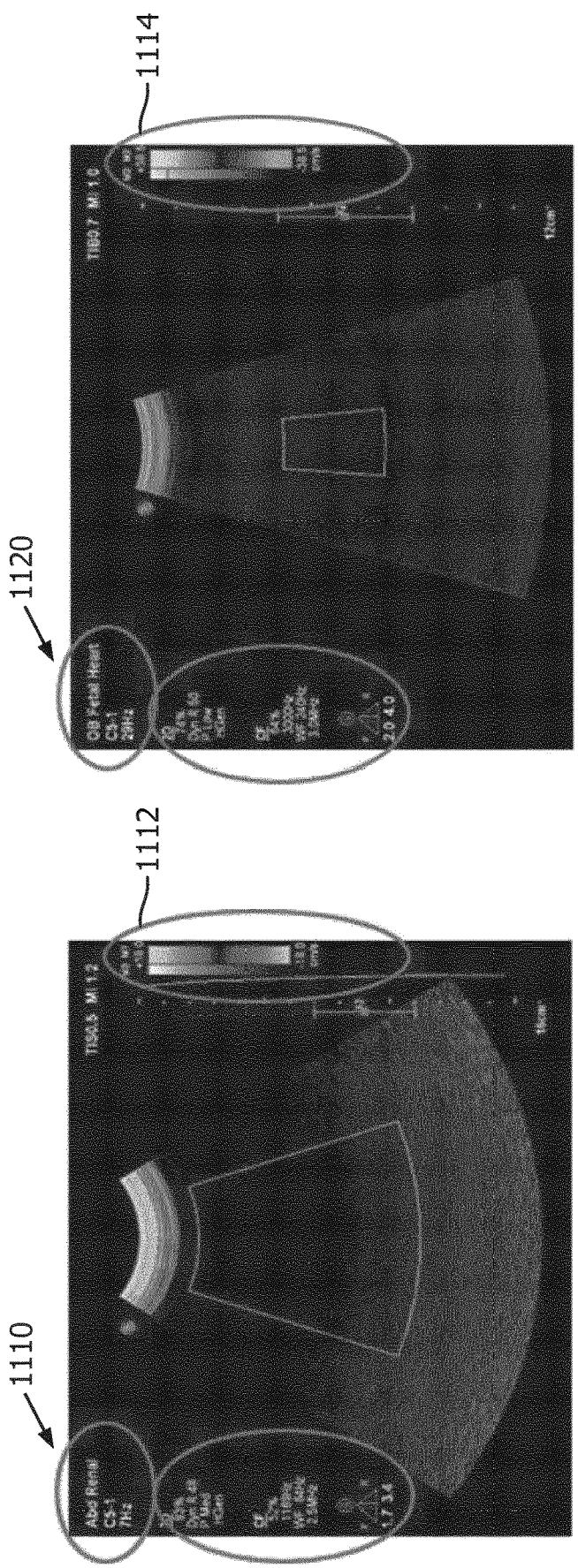
FIGS. 11A and 11B show ultrasound images of two different types of tissue and corresponding imaging settings suitable for imaging the illustrated types of tissue.
Figure 12A:
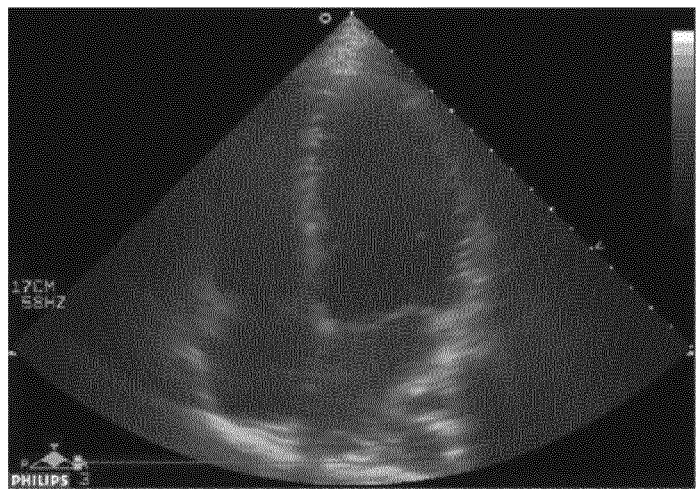
FIGS. 12A, 12B and 12C shows examples of ultrasound images which illustrate the effect of usage of the correct or incorrect imaging parameters on the quality of the image.
Figure 12B:
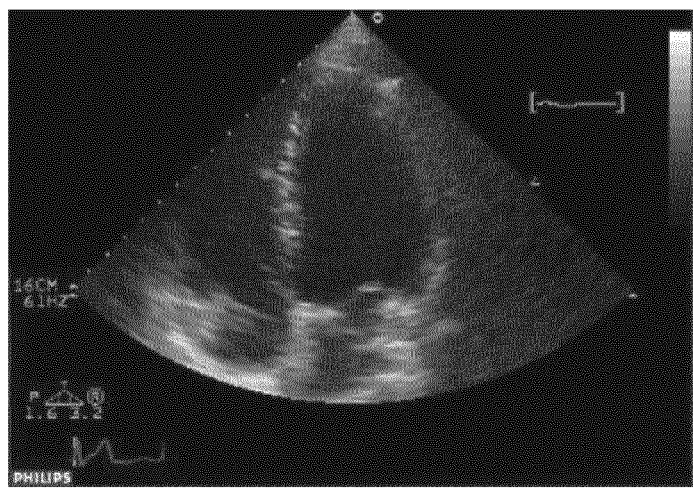
Figure 12C:
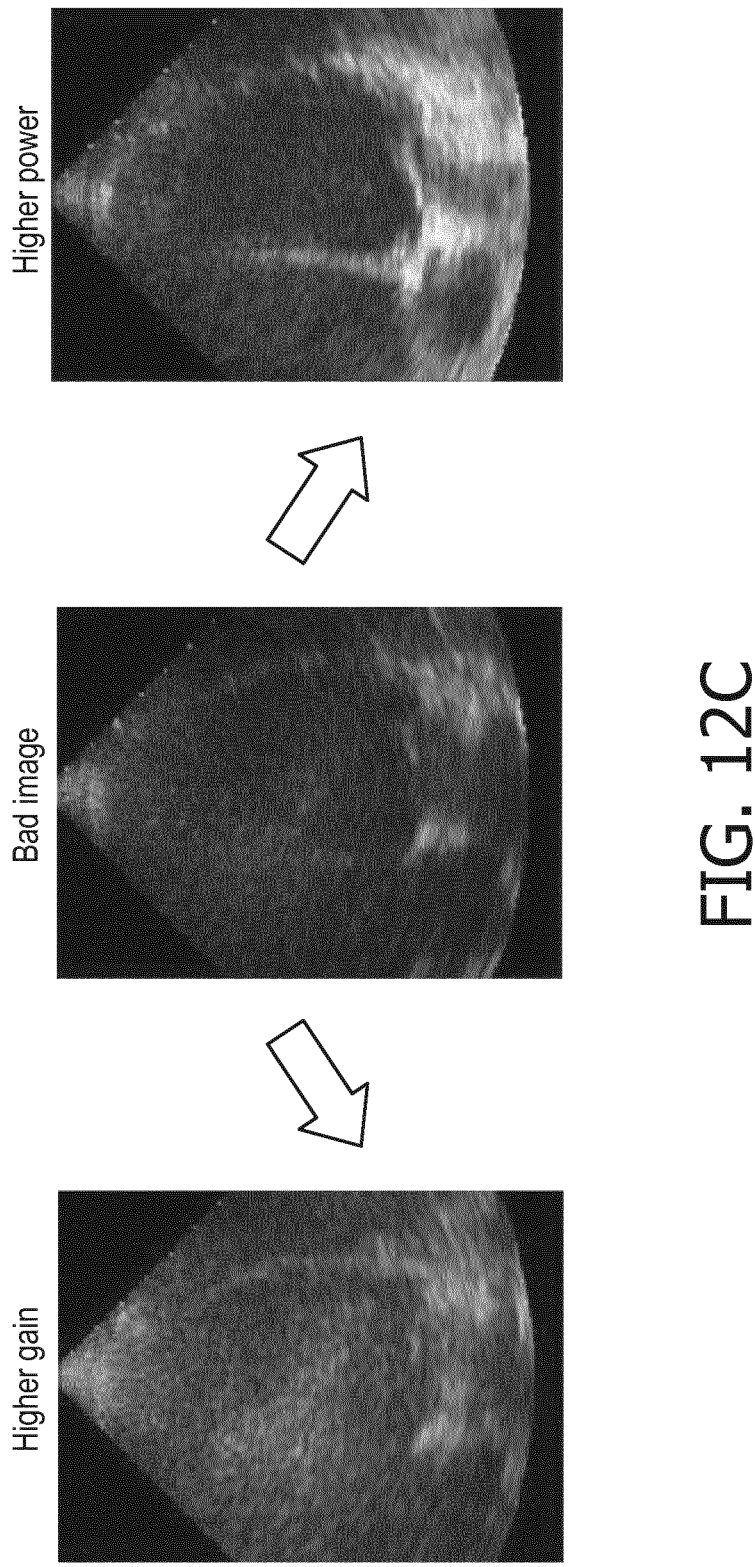

The imaging parameter settings may control qualitative aspects of imaging (e.g., dynamic range for display, depth, imaging frequency, etc.) and quantitative aspects of imaging (e.g., flow velocity), and the ideal qualitative and quantitative imaging parameters may vary from organ to organ. For example, as shown in FIGS. 11A and 11B, the blood flow velocities (see ranges 1112 and 1114) associated with an abdominal renal preset (1110 in FIG. 11A) and an OB cardiac preset (1120 in FIG. 11B) are very different. More specifically, for abdominal renal imaging, the blood flow range 1112 may be about ±18 cm/s, while in an OB Fetal Heart exam the blood flow range 1114 may be much higher, up to about ±38.5 cm/s. When quantitative measurements are performed, the range of blood flow velocities is an important parameter that needs to be set accurately in order to avoid aliasing artefacts in Doppler images. Aliasing occurs when the peak velocity of the blood flow is faster than the Doppler frequency shift that is set on the Doppler scale. Thus, selecting the appropriate preset with the correct blood flow range ensures that the appropriate pulse sequences with appropriate pulse repetition frequency (sampling rate) will be used during imaging. If instead an incorrect preset is used and an aliased signal is recorded, the peak flow velocity will be cut-off in the aliased signal, introducing error and potentially leading to misdiagnosis. FIGS. 12A-C show further examples of cardiac images, which illustrate the effect of incorrect imaging parameters of the output images. FIG. 12A, shows a relatively poor quality image, with manifestations of blurred cardiac walls, low image contrast and strong clutter artefacts, caused by the wrong use of abdominal TSP. FIG. 12B shows improved image quality by the selection of the correct preset and thus applying the appropriate imaging parameter settings. FIG. 12C illustrates that even with an appropriately selected preset for a given imaging application, further fine tuning of the settings applied by a preset may improve the organ-specific settings for a further improvement in image quality, which may be achieved with an adaptive TSP model according to the present disclosure.

The TSPs available on ultrasound scanners use population based settings provided by manufacturer. Once the selection is made by the user, they very often have to keep adjusting the parameters to match each patient's acoustic properties. Due to presence of wide varieties of TSPs in the imaging systems, a user can inadvertently use a preset during examination which is not ideal or optimal for the particular imaging application. For example, in urgent care settings where time can be critical, clinicians may not have the time to switch TSP when examining different organs. In addition, users often tailor the pre-programmed imaging parameters for each patient accordingly to their own preferences in interpreting and reading the ultrasound images. Different users may chose very different settings for the same patient, and sometimes a user may save customized system setting as their go-to TSPs. These custom or user-specific TSPs may, in some cases, be preferred by a given user over the pre-programmed (factory default) TSPs.

As described above, many types of transducers are available for use in ultrasound examination. For example, different types of transducers may be designed for imaging different organs of the body and/or for specific clinical applications. In some cases, the same transducer may be used for imaging different organs and may be equipped with several exam-specific imaging presets. In everyday practice of ultrasound sonography, the sonographer has to make a preselection of initial imaging settings to start the ultrasound examination, hence a TSP selection is typically required before starting any exam. Users have to usually go through the whole list of available pre-sets and then pick one for the current exam. Additionally, because the available TSPs are based on a general population (e.g., the factory default presets are typically optimized for use a wide variety of patients), the sonographer may have to adjust the settings of the selected preset with various buttons and knobs on the scanner to find the right combination of imaging parameters for the current patient. These procedures can be time consuming and particularly undesirable in urgent care setting where time is generally critical and this type of reconfiguration of the system during the exam would take up valuable time that should otherwise be dedicated to caring for the patient.

An ultrasound imaging system according to the present disclosure may be configured to detect an incorrectly selected preset and to automatically apply the correct preset, the correct preset being the preset determined by the system to be the optimal preset for the current scan (e.g., best suited for the current probe, imaging application or organ, patient, user, etc.). The automatic selection of a correct preset may be achieved by first identifying the type of organ being imaged and then retrieving an appropriate preset for the organ. This identification and preset selection may be performed periodically during an exam, e.g., continuously while the patient is being scanned such that if the sonographer moves to imaging another organ without switching the preset, the system would automatically detect the change and apply the appropriate preset.

In some examples, the system may be further configured to adapt or adjust the settings of imaging parameters of the system (e.g., the settings applied by a given TSP) to settings that are determined by the system to be better suited for the particular patient being examined and/or to those determined by the system to be better suited for the current operator of the system (e.g., the sonographer performing the exam). To that end, the system may be configured to identify user-specific settings (e.g., retrieve and isolate custom settings associated with the specific current user) and patient-specific settings (e.g., settings previously used for the same patient and same organ) from a data store containing previous settings and to automatically adjust the current settings to the retrieved user-specific and/or patient-specific settings. The term organ detection or identification may imply identification of a specific organ (e.g., the heart or liver) or more generally the type of tissue (e.g., renal, hepatic, vascular, breast tissue, etc.) being examined.

Figure 1:
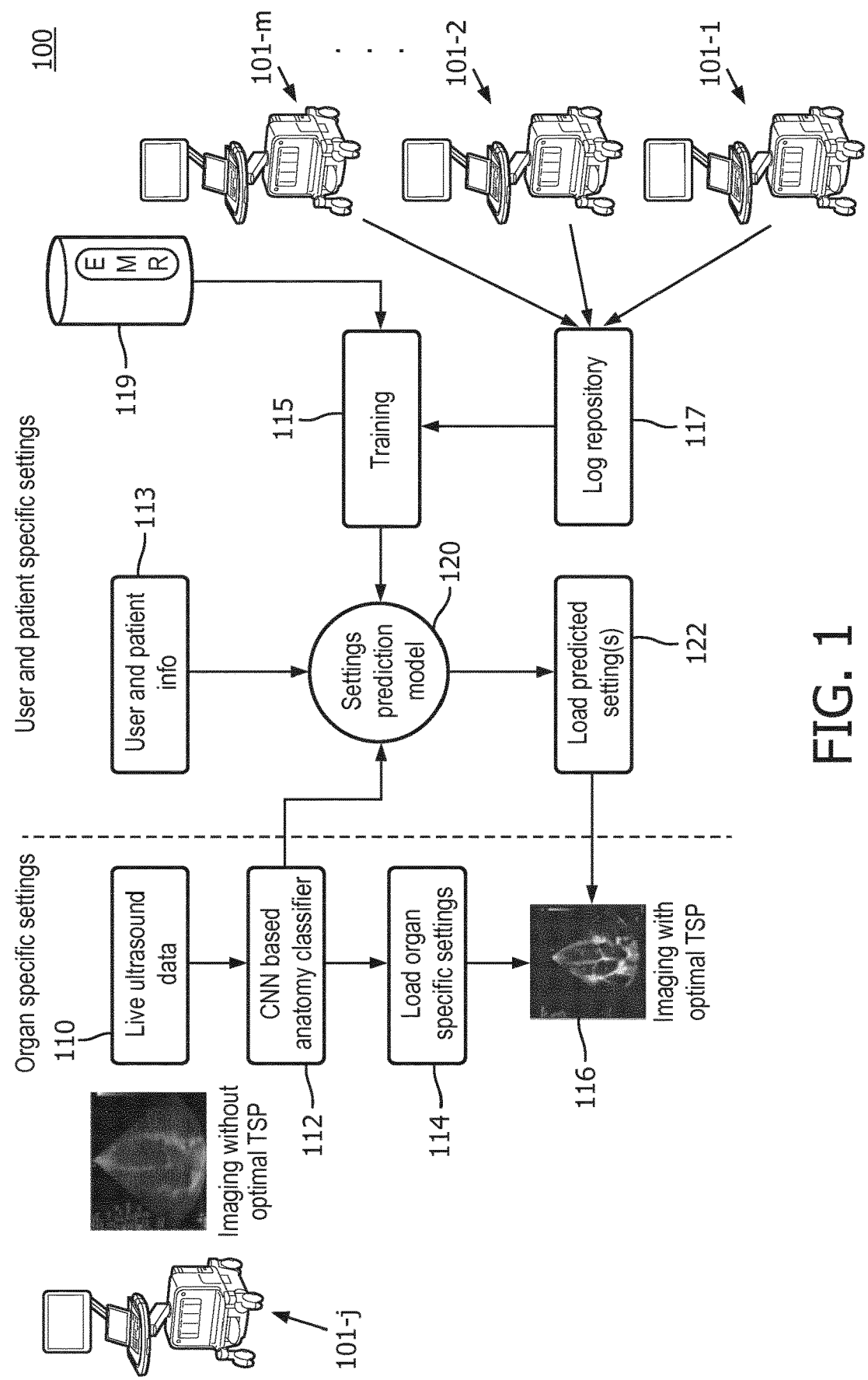
FIG. 1 shows a flow diagram of a process for ultrasonically inspecting biological tissue in accordance with some examples of the present disclosure.

FIG. 1 shows a flow diagram of an example process 100 for automatically reconfiguring (e.g., adjusting imaging parameter settings) of an ultrasound imaging system (e.g., ultrasound scanner 101-*j*) during live imaging in accordance with the principles of the present disclosure. The ultrasound scanner 101-*j* may be configured to acquire and generate live images of biological tissue from ultrasound transmitted toward the biological tissue. As shown in FIG. 1, initially, images may be acquired with imaging settings which may not be ideal for the given imaging application. As described, in addition to performing conventional signal and image processing of the echo signals (e.g., for the purpose of producing images), the system may also, in parallel, couple one or more of the live images to a processor for identification of the type of tissue that is being imaged. The identification of the type of tissue may be used by the system for automatic selection and application of tissue-specific imaging parameters so as to obviate the need for the operator to manually switch between presets when moving to a new area of the anatomy. The process 100 may begin, at block 110, by receiving an ultrasound image in a processor, which implements a tissue identification module (also referred to as detection module) configured to identify the type of tissue being imaged. The tissue identification module may be implemented using at least one appropriately trained artificial neural network (or machine-learning model). The processor of ultrasound scanner 101-*j* may use a machine-learning model having any suitable architecture (e.g., a convolutional neural network as shown in the example in FIG. 1) which is trained for the task of identifying the type of tissue that is represented in the input ultrasound image. The machine-learning model may reside on the ultrasound scanner 101-*j* or on a remote computing device communicatively coupled to the ultrasound scanner 101-*j*.

The process continues, at block 112, by identifying the type of tissue being imaged and selecting a tissue specific preset for the identified type of tissue. As described, the identification may be performed by a processor residing on the ultrasound scanner 101-*j*, which implements (i.e., executes processor executable instructions) a machine-learning classification model. In some examples, the identification may be performed by a remote (e.g., networked or cloud-based) processor, and the identification of the tissue type may be received, in real time, by the local processor of the ultrasound scanner 101-*j*. At block 114, the tissue-specific preset selected based on the identified type of tissue is automatically applied to adjust the imaging parameter settings of the ultrasound scanner 101-*j* for subsequent live imaging (at block 116). Thus, subsequent live imaging (e.g., acquisition and display of image data) by the ultrasound scanner 101-*j* (at block 116) occurs using the automatically reconfigured imaging settings. As described, process 100 may run in the background in real-time (i.e., while a live scan of the subject is being performed), thus as the operator moves the probe to image different anatomy of the subject, the system identifies, in real time, the anatomy being represented in the image data, selects an appropriate TSP, and automatically applies the settings defined by the TSP to adjust the imaging parameters of the system without requiring involvement by the user (i.e., manual selection of a TSP or manual adjustments of individual settings) thus freeing up the user's attention to patient care.

As further shown in FIG. 1, reconfiguration of the system based on organ detection may be alternatively or additionally involve automatic reconfiguration of the system, based on predicted settings. The predicted settings may be settings which the system determines, for example with the use of an appropriately trained neural network, corresponding to preferred or optimal settings for the particular user and/or patient. In some examples, the predicted settings may be applied following a selection of a TSP, as described above, such as to further fine tune the imaging settings of the ultrasound scanner 101-*j*. In some examples, the step of selecting and applying a TSP may be omitted and the tissue identification may solely be used to initiate the settings prediction process as described herein. For example, the tissue identification may be a precursor step to the prediction process as the type of tissue may be an input to the settings prediction model. In some examples, the tissue identification may be followed by a selection of an appropriate TSP and the settings defined by the TSP may be used as input to settings prediction model alternatively to or in addition to the type of tissue. The setting prediction model 120 may include at least one neural network, which implies one or a plurality of appropriately arranged neural networks and trained to output imaging parameter settings that correspond to user-preferred and/or patient-specific settings. These user-specific settings, patient-specific settings, or a combination thereof (collectively referred to as predicted settings) may be automatically applied (at block 122) to the ultrasound scanner 101-*j* such that subsequent live imaging by the system occurs in accordance with the predicted settings, until further adjusted by the user or the system. As described, in one example, upon identification of the tissue type at block 112, the type of tissue as well as user identification and patient identification information if provided to a settings prediction model (block 120). The settings prediction model 120 may be implemented using any suitable artificial neural network architecture (e.g., machine-learning regression model) appropriately trained to predict one or more preferred settings. This model 120 may be trained, in some examples, using historical data (e.g., system logs from multiple prior scans performed by the same operator and/or of one or more recurrent patients). The settings prediction model 120 may be configured to receive, as inputs, any combination of the user identification information, patient identification information (as shown at block 113), tissue type, and one or more of the settings defined by a TSP. The user identification information may include, for example, a user ID which may be keyed in or provided by the user by some other means (e.g., via voice input, a biometric scan, or scanning the user's badge), such as at the start of the exam. The patient identification information may include any information that may be used to identify the patient such as patient name, medical records ID, date of birth, etc., which information may also be input by the user or received by the ultrasound system in other ways as described further below. One or more predicted settings for one or more corresponding imaging parameters are output by the settings prediction model at block 120 and the predicted settings are automatically applied to the ultrasound scanner 101-*j* to affect subsequent live imaging with the ultrasound scanner 101-*j*.

Thus, a method of ultrasonically inspecting biological tissue in accordance with the principles of the present disclosure may include receiving, in real-time, by a processor of an ultrasound system, an ultrasound image from a live stream of ultrasound images, receiving an identification of a type of the biological tissue in the ultrasound image, selecting one of a plurality of presets stored in a memory of the ultrasound system based on the type of the biological tissue in the ultrasound image, automatically adjusting one or more imaging parameters of the ultrasound system to settings defined by the selected preset, based on the type of the biological tissue, identifying, using an artificial neural network, one or more user-specific settings, patient-specific settings, or a combination thereof for at least one of the one or more of the imaging parameters, and automatically adjusting the at least one imaging parameter in accordance with the one or more user-specific settings, patient-specific settings, or the combination thereof for subsequent live imaging.

As further shown in FIG. 1, the process 100 may also include training (at block 115) of the settings prediction model 120. The model 120 may be trained using data extracted from patient records, which may be stored in an electronic medical records database 119, as well as data extracted from system logs produced by a number of ultrasound imaging systems (e.g., ultrasound scanners 101-1, 101-2, through 101-*m*, which may include the ultrasound scanner 101-*j*). The system logs may be stored in any suitable data storage device (e.g., a log repository 117, which may be part of the picture archiving and communication system of the medical facility or any combination of wired or wirelessly networked data storage devices).

Figure 2:
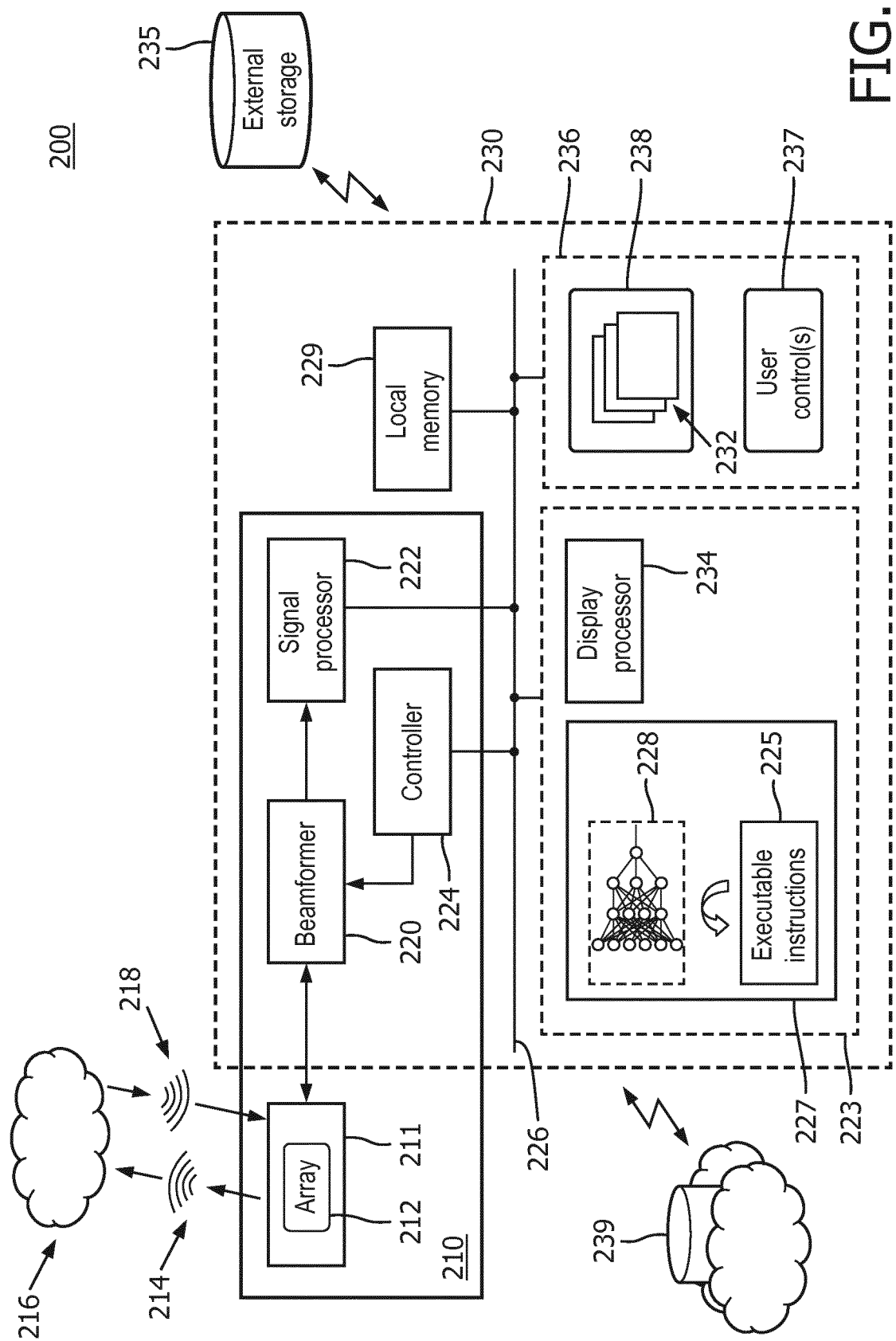
FIG. 2 is a block diagram of a system according to the principles of the present disclosure.

FIG. 2 shows a block diagram of a system 200 in accordance with some examples of the present disclosure. The system in FIG. 2 may embody, at least in part, and be used to perform the process 100 or any sub-processes thereof. FIG. 2 shows an ultrasound data acquisition unit 210 including an ultrasound transducer or probe 211, a beamformer 220, a controller 224, and a signal processor 222. FIG. 2 also shows a user interface 236 including a display 238, a memory 229, and at least one image data processor 223 all communicatively coupled to the ultrasound data acquisition unit 210, e.g., via a data bus 226. The components of system 200 and the arrangement thereof shown in FIG. 2 are illustrative only and variations, such as combining, rearranging, adding, or removing components are contemplated.

The ultrasound data acquisition unit 210 may be configured to acquire ultrasound image data 232, which may be displayed, responsive to processor 223, on the display 238 in real-time (i.e., as the image data is being acquired by ultrasonically scanning the subject). Thus the processor 223 may be configured to generate and cause the system, namely display 238, to display, in real-time, a live stream of ultrasound images of biological tissue 216. The images are generated and displayed in accordance the imaging parameters of the ultrasound system (e.g., depth, focus, gain, dynamic range, etc.). The system may also be operated in a manner (e.g., capture mode) in which a portion of the live stream is concurrently recorded in a cineloop in the memory 229 of the system, e.g., for future, off-line inspection. The system 200 may be communicatively connected (e.g., via a wired or wireless connection) to an external storage device 235 for retrieving image data or other information and for longer-term storage of acquired image data (e.g., still images or cineloops). In some examples, external data may be retrieved for and storage may also be provided by a cloud-based computing device 239.

The ultrasound data acquisition unit 210 may include some or all of the components of a typical ultrasound scanner. For example, the ultrasound data acquisition unit 210 may include an ultrasound transducer or probe 211, which includes an ultrasound sensor array 212. The sensor array 212 is configured to transmit ultrasound 214 toward and detect echoes 218 from biological tissue 216, e.g., liver, kidney, breast, cardiac tissue or other types of biological tissue of a subject, for ultrasonically imaging the tissue 216. Different types of tissue may be scanned in different exams, and the system 200 may thus be configured to receive (e.g., responsive to user inputs and/or processor-conducted image data analysis) an indication of the type of tissue, in preferred examples, the determination of the type of tissue being made by the ultrasound system 200.

A variety of transducer arrays may be used, e.g., linear arrays, curved arrays, or phased arrays. The array 212, for example, can include a two dimensional array of transducer elements capable of scanning in both elevation and azimuth dimensions for 2D and/or 3D imaging. The ultrasound data acquisition unit 210 includes a signal processor 222, which may be housed with the sensor array 212 or it may be physically separate from but communicatively (e.g., via a wired or wireless connection) coupled thereto. For example, the array 212 may be located in a handheld probe while the signal processor 222 may be located in the ultrasound system base 230, which in some cases may be embodied in a portable computing device such as a tablet.

The array 212 may be coupled to the system base 230 via a beamformer 220 configured to control operation of the array 212. In some embodiments the beamformer 220 may include one or more beamformers, (e.g., a microbeamformer in combination with a main beamformer in the ultrasound system base, or a combination of transmit and receive microbeamformers and/or main beamformers). The beamformer 220 may be configured to control the transmission of ultrasound and reception of echo signals by the array 212. In some embodiments, the beamformer 220 may include a microbeamformer, which may be co-located with the ultrasound array in the probe, and operating on groups of sensor elements for the transmission and/or reception of signals by the groups of sensor elements of the ultrasound sensor array 212. In some embodiments, the microbeamformer may be coupled to a transmit/receive (T/R) switch (not shown), which may be configured to switch between transmission and reception to protect the main beamformer from high energy transmit signals. In some embodiments, for example in portable ultrasound systems, the T/R switch and other elements of the system can be included in the ultrasound probe rather than in the system base 230. The ultrasound base typically includes software and hardware components including circuitry for signal processing and image data generation as well as executable instructions for providing a user interface. In some embodiments, the ultrasound probe may be coupled to the ultrasound system base via a wireless connection (e.g., WiFi, Bluetooth) or via a wired connection (e.g., a probe cable, which may be configured for parallel or serial data transmission).

The system 200 may include one or more processing components for generating ultrasound images from echoes detected by the array 212. For example, the system 200 may include a signal processor 222 may be configured to process the echo signals received from the transducer 211 for generating ultrasound image data and at least one image data processor 223 for presenting the ultrasound image data (e.g., ultrasound images 232) on the display 238 of system 200. The ultrasound data acquisition unit 210 may include or be operatively coupled to a user interface 236, which may be integral with or otherwise physically connected to the system base 230 that houses the signal processor 222. In some embodiments, at least some components of the user interface may be wirelessly connected to the signal processor 222.

The user interface 236 may include a display 238 for displaying the ultrasound images 232 and in some cases, interactive graphical user interface (GUI) components. The user interface 236 may also include one or more user controls 237 for controlling operation(s) of the system 200. In some embodiments, the user control(s) 237 may include one or more hard controls (e.g., buttons, knobs, dials, encoders, mouse, trackball or others), which may be provided on a control panel of the system base 230. In some embodiments, the user control(s) 237 may additionally or alternatively include soft controls (e.g., GUI control elements or simply, GUI controls) provided on a touch sensitive display. The system 200 may also include local memory 229. The local memory may be provided by one or more hard disk drives, solid-state drives, or any other type of suitable storage device comprising non-volatile memory. The local memory 229 may be configured to store image data, executable instructions, or any other information necessary for the operation of system 200. In some examples, the system 200 may also be communicatively connected (via wired or wireless connection) to external memory (e.g., storage 235, such as a storage device of a picture archiving and communication system (PACS), cloud-based computing device 239, or a combination thereof).

The signal processor 222 may be communicatively, operatively, and/or physically coupled to the sensor array 212 and/or the beamformer 220. The signal processor 222 may be configured to receive unfiltered and disorganized ultrasound data representing the ultrasound echoes 218 detected by the sensor array 212. From this data, the signal processor 222 is operable to generate ultrasound image data, which may be appropriately arranged, e.g., by processor 223, into images 232 for display. For example, the signal processor 222 may be configured to process the received echo signals in various ways, such as bandpass filtering, decimation, I and Q component separation, and harmonic signal separation. The signal processor 222 may also perform additional signal enhancement such as speckle reduction, signal compounding, and noise elimination. The signal processor 222 may then produce B-mode image data from the component signals such as by employing amplitude detection or any other known or later developed technique for the imaging of structures in the body. The B-mode image data may be further processed by scan conversion, e.g., to arrange the signals in the spatial relationship from which they were received in a desired image format. For instance, the scan conversion may arrange the signals into a two dimensional (2D) sector-shaped format, or a pyramidal or otherwise shaped three dimensional (3D) format. The B-mode image data may alternatively or additionally be processed by a multiplanar reformatter, which is configured to convert echoes which are received from points in a common plane in a volumetric region of the body into an ultrasonic image (e.g., a B-mode image) of that plane, for example as described in U.S. Pat. No. 6,443,896 (Detmer). The one or more processors of system 200 (e.g., processor 222 or 223) may additionally or alternatively generate a volume rendering of the B-mode image data (i.e. an image of the 3D dataset as viewed from a given reference point), e.g., as described in U.S. Pat. No. 6,530,885 (Entrekin et al.).

The signal processing and generation of image data may be performed in real-time as an operator ultrasonically scans the tissue 216 such that the image data may be displayed as real-time (or live) images of the subject. Alternatively, the images 232 may be generated from previously acquired image data stored in memory (e.g., local or external memory) associated with system 200. As described, the ultrasound data acquisition unit 210 may include a controller 224, which may be configured to set imaging parameters of the system 200, e.g., to control the transmission and reception of signals by the array 212, as well as certain signal and image processing functions of the system 200. The controller 224 may, among other things, control or set the imaging parameters of the system 200, which settings may be utilized by the beamformer 220 in controlling the excitation of elements of the array for the transmission and detection of signals by the array 212. Settings applied by controller 224 may also affect the signal and image processing of acquired ultrasound data, e.g., by controlling compressed dynamic range for display of images, or other image processing or display settings. As described, the transmission of ultrasonic pulses from the transducer array 212 under control of the beamformer may be directed by the transmit/receive controller, which may be coupled to the T/R switch and which may receive input from the user's operation of the user interface 236. Another function, which may be controlled by the controller 224, is the direction in which beams are steered, in the case of an electronically steerable array. Beams may be steered straight ahead from (orthogonal to) the transducer array 212, or at different angles for a wider field of view.

As shown in FIG. 2, the data acquisition unit 210 may be communicatively connected to at least one processor 223 configured to perform one or more of the functions associated with the intelligent (also referred to as computer-assisted, or AI-assisted) scanning of biological tissue, for example for the automatic and dynamic reconfiguring of the imagining parameters of the system based on the tissue being scanned, without necessarily requiring operator involvement in the setting of imaging parameters. The processor 223 may include one or more processing units (e.g., one or more single or multi-core CPUs, a single GPU or GPU cluster, or any arrangement of multiple processors configured for example for parallel processing) and uniquely configured to perform the functions described herein. For example, the processor 223 may be further configured to receive, in real-time, an ultrasound image from the live stream of ultrasound images acquired by the ultrasound data acquisition unit 210, receive an identification of a type of the biological tissue in the ultrasound image (e.g., responsive to user inputs and/or automated image data analysis performed by processor 223, as further described herein), and based on the type of the biological tissue, generate, using an artificial neural network 228, at least one predicted setting for at least one of the plurality of imaging parameters. The processor 223 may then automatically apply the at least one predicted setting to the respective imaging parameter for subsequent live imaging. For example, the processor 223 may send commands to the controller 224 to change acoustic settings of the system, such as the depth, focus, transmit and/or receive frequencies, etc. or to the signal processor 222 and/or other components of the system used in converting the echo signals into image data for adjusting other imaging parameters, such as the TGC or velocity ranges (e.g., in the case of Doppler imaging) to adjust the imaging parameters of the system in accordance with the predicted setting(s) such that the predicted setting(s) are automatically used by the system in subsequent live imaging, until further adjusted by the system or the operator.

In addition to performing functions associated with intelligent scanning of biological tissue, the processor 223 may be configured to provide other functionality associated with the display of image data are related information. In some embodiments, the processor 223 may include a display processor 234, which may additionally include functionality for generating and causing the display 238 to present annotations along with the image data, such as annotations identifying the preset selected, any adjustments made to the preset such as by highlighting those imaging parameters that were tuned by the artificial neural network, and/or simply listing one or more of the imaging parameters used to produce the image being displayed (e.g., in real time). The annotations may also be saved (e.g., stored with the image, either as annotations on the image and/or as metadata accompanying the stored image). In embodiments herein, the display processor 234 may receive the image data for further enhancement, buffering and temporary storage before being displayed on display 238. The display 238 may include a display device implemented using a variety of known display technologies, such as LCD, LED, OLED, or plasma display technology. While the engine 227 and display processor 234 are shown as separate components in FIG. 2 for illustration, in practice the functionality of these components (and any other processing components described herein) may be integrated into a single processor or a cluster of processors arranged to operate together (e.g., in parallel).

As will be further described, the processor 223 may include a settings prediction engine 227, which may be embodied in any suitable combination of software (e.g., executable instructions in the form of source code or compiled/machine instructions) and hardware components (e.g., one or more processors programmable by the executable instructions and/or hard-wired circuitry such as application specific integrated circuits ASICs specifically programmed to perform one or more of the functions of engine 227). The engine 227 may include functionality for preforming one or more of the steps described with reference to FIG. 1 or any other processed described herein. In some examples, the functionality of engine 227 may be implemented via processor-executable instructions 225, which when executed by processor 223 configure or program the processor to perform the functions associated with generating predicted settings (e.g., settings determined by the system to reflect patient-specific and/or user-specific preferences) and automatically causing those settings to be applied to the imaging system 200. In some embodiments, as described further herein, the engine 227 may include at least one artificial network of neural perceptrons 228 (also referred to herein as artificial neural network or simply neural network), trained to perform one or more of the functions of engine 227. Any suitable types of machine-learning algorithms or models (e.g., generative, discriminative, generative adversarial, classification, regression, convolutional, or any combinations thereof) with any suitable architecture (e.g., configuration of interconnected layers) may be used to implement the neural network 228. In some such embodiments, the neural network 228 may implement a machine-learning regression model which is trained, based on historical data (e.g., from system log files of prior scans) to identify suitable patient-specific and/or user-specific settings for any given imaging scenario. The neural network 228 may have any suitable architecture, and thus include any suitable number of layers of input, output, and hidden nodes in any suitable arrangement (e.g., layers of convolution, normalization, pooling, and/or fully connected layers). In some examples, the network 228 may include an arrangement of one or more subnetworks forming a larger network trained to produce the desired result(s). In yet further examples, the neural network 228 may be operatively associated with additional programming, e.g., to perform pre-processing of the input data and/or post-processing of the output of the network 228 for use by imaging system 200.

As described, some or all of the components of system 200 may be co-located (e.g., within a system base 230) and communicatively connected (e.g., via a data bus 226). Additionally or alternatively, components of the system 200 may be connected to remote components via one or more wired or wireless connections. For example, the system base 230 may additionally be communicatively coupled to external storage 235, e.g., an external drive or a PACS storage device of the medical facility. In some embodiments, some or all of the functionality one or more neural networks used by the imaging system 200 may reside in a remote computing device 239, such as a cloud server, which may be communicatively coupled to the system base 230 (for example a portable system such as a tablet-based U/S scanner) configured to transmit the live images to the cloud for classification and/or other analysis and to receive the output of the classification or analysis (e.g., identification of tissue type) for selection of a TSP and/or for automatic reconfiguring of the system 200.

Figure 3:
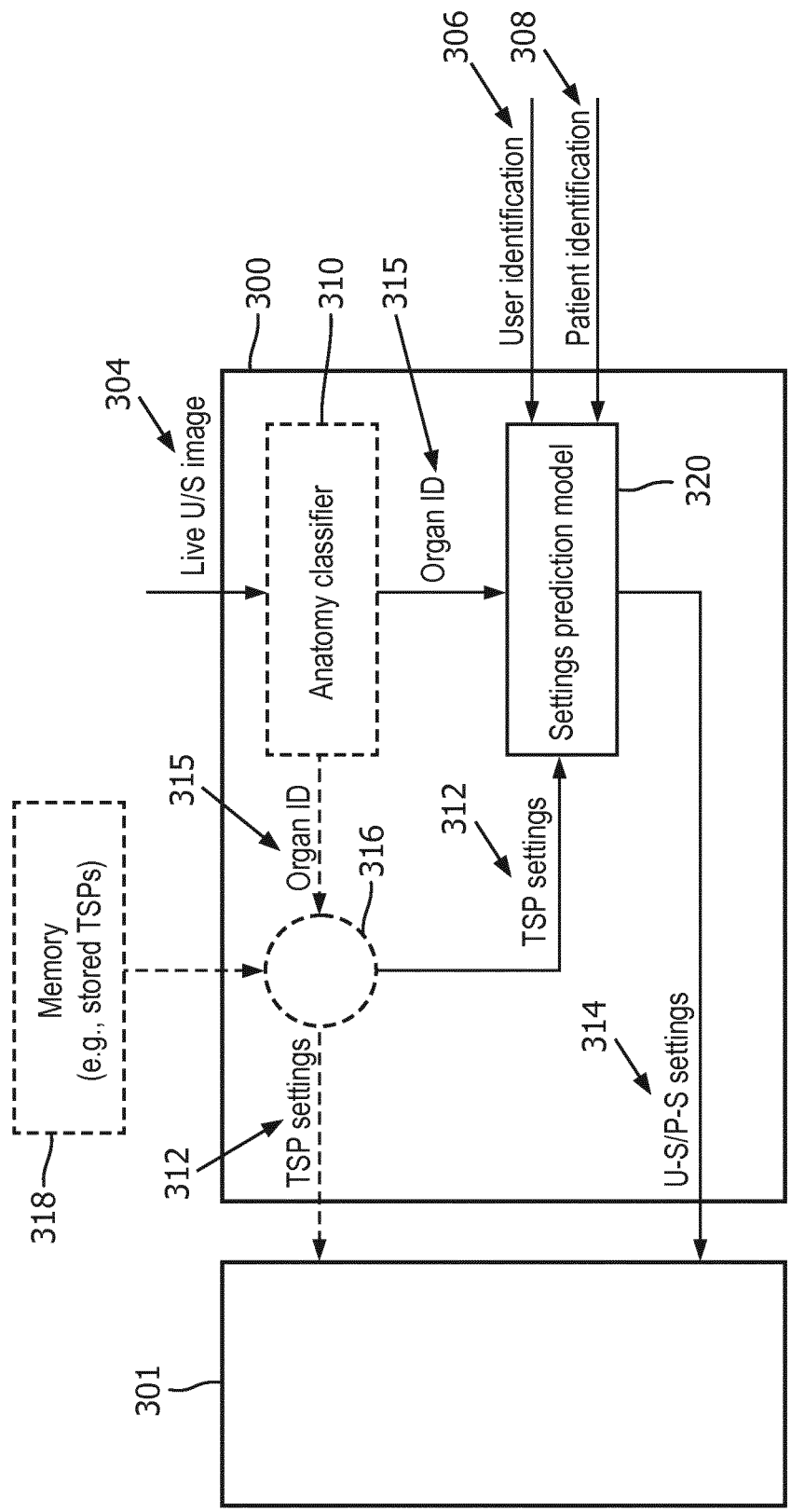
FIG. 3 is a block diagram of a processor for an ultrasound imaging system according to the present disclosure

As described herein, in some examples the identification of the biological tissue may be performed by the processor 223, for example using a machine-learning model, such as properly trained machine-learning organ classification model. Thus, while only a single neural network 228 is shown, for purposes of illustration, in FIG. 2, it will be understood that processor 223 may use a plurality of appropriately connected neural networks which may have different architectures and may be trained for different end results. For example, as shown in FIG. 3, a processor 300 may include (or communicate with) a neural network 310 trained as an anatomy classifier, and another neural network 320 trained as a setting(s) predictor. The neural network 310 may be configured to output an identification of the type of biological tissue being imaged (e.g., organ identification 315), which is coupled to the second neural network 320 for setting(s) prediction. Tissue type identification may be performed by an appropriately trained neural network, such as a convolutional neural network trained to classify ultrasound images based upon the type of tissue included in the image.

In some examples, the system may optionally include memory (e.g., local memory 229, which can include any suitable type of non-volatile memory (e.g., read-only memory, programmable read-only memory, electrically erasable programmable read-only memory, flash memory, random-access memory, or any other type of suitable non-volatile memory) that stores a plurality of presets (i.e. tissue-specific presets or TSPs). Each preset may include or define an ensemble of imaging parameter settings that have been determined (e.g., through testing) to be suitable for imaging a given type of tissue. In some embodiments, the processor 223 may be configured to select one of the plurality of stored presets based on the type of the biological tissue and to automatically apply the selected preset to adjust one or more of the plurality of imaging parameters of the system to settings defined by the selected preset, for example, prior to or while predicted settings are being generated. In some examples, the settings defined by the selected preset may be used as inputs to the neural network 228. In such examples, the neural network 228 may be trained to output the user and/or patient-specific settings associated with any given selected TSP, and thus the neural network 228 may be viewed as tailoring or fine-tuning the preset to the operator's preferences without any operator involvement.

Referring further to FIG. 3, an example processor 300 for an ultrasound imaging system is described. Processor 300 may be used to implement one or more of the processors (e.g., processor 223) of an ultrasound imaging system according to the present disclosure (e.g., system 200). As shown in FIG. 3, processor 300 receives, as input, an ultrasound image 304, which may be coupled to processor 300 in real-time (e.g., during live imaging). That is, the term "live ultrasound image" may be used to refer to an ultrasound image from a live stream of images acquired by the system.

The processor 300 may include an anatomy classifier 310 configured to identify the type of biological tissue represented in the received image 304. In some examples, the anatomy classifier 310 is implemented using a machine-learning model, for example a machine-learning classification model such as in the example in FIG. 5. As described, the anatomy classifier 310 is configured to identify the type of biological tissue represented in the ultrasound image 304 and to transmit the identification 315 to the settings prediction model 320. In some embodiments, such as in the case of a machine-learning model, the anatomy classifier 310 may be trained to classify an input ultrasound image into one or a plurality of possible tissue or organ classifications. In other embodiments, the tissue identification may be obtained differently, e.g., by any suitable image processing technique (e.g., segmentation) other than machine-learning, or responsive to user input, for example by voice input of the operator audibly identifying the anatomy being scanned as the operator moves the probe to a new location.

The tissue type identification may be coupled to a settings prediction model 320, which is configured to output a set of imaging parameters predicted or determined by the processor, for example based upon training, to be suitable for imaging that type of tissue. Thus, in preferred embodiments, the settings prediction model 320 may be implemented using at least one appropriately trained machine-learning model (s), for example using a machine-learning regression model (e.g., as described with reference to FIGS. 6-9). The settings prediction model 320 may receive, as input(s), any combination of the tissue type, user identification information, patient identification information, and one or more current imaging settings of the system. In the example in FIG. 3, the settings prediction model 320 receives, as input, the tissue type 315, as well as user identification input(s) 306, patient identification input(s) 308, and the current settings (e.g., the TSP settings 312 selected automatically by the system or responsive to user input). As described herein, the settings prediction model 320 is trained to output one or more predicted settings 314, which may then be automatically applied to reconfigure the ultrasound imaging system, such as by coupling them to one or more controllers 301 of the system. As the processor 300 performs tissue type identification and settings prediction in the background, the need for operator involvement in setting the appropriate imaging parameters may be obviated and/or the processor may function to double-check that an appropriate imaging setting has been selected. In the case of the latter, if the processor 300 determines that a different set of imaging parameter settings should be applied rather than the selected settings, and the processor 300 is not operating in an automatic reconfiguration mode, the system (e.g., system 200) may additionally, optionally, provide user feedback to warn the user that they may be imaging with incorrect settings.

In some embodiments, the patient identification input(s) 306 may be obtained in accordance with any of the examples in co-pending patent application titled "Ultrasound system with artificial neural network for retrieval of imaging parameter settings for recurring patient," the content of which is incorporated herein by reference in its entirety for any purpose. For example, the processor 300 may additionally implement or be communicatively coupled to at least one additional neural network trained to identify a recurring patient based upon patient identification information received by the system. The recurring patient may be associated with a patient ID and thus the patient identification input 308 may correspond to the patient ID. The settings prediction model 320 may thus be operable to output predicted settings 314 based at least in part on the patient identification input 308. In some examples, the patient ID and/or other patient identifying information (e.g., height, weight, BMI, name, date of birth, age, sex, medical record ID, etc.) may be provided to the system (e.g., to processor 300) responsive to user inputs. In some examples, the settings prediction model 320 may be configured to receive any combination of the patient ID and/or other patient identifying information (e.g., height, weight, BMI, name, date of birth, age, sex, medical record ID, etc.) as the patient identification input(s) 308 and to output predicted settings based, at least in part, on the patient identification input(s) 308. In some embodiments, the settings prediction model 320 may include a cascading network (i.e. plurality of appropriately connected sub-networks), a portion of which is trained to perform patient identification based upon, patient identification information such as patient height, patient weight, patient BMI, patient name, date of birth, age, sex, patient medical record ID, etc., and which is operatively connected with other portions(s) of the cascading network to supply the patient identification thereto for settings prediction.

Referring back to FIG. 3, the processor 300 may be configured to optionally select a pre-stored TSP (at selection block 316) based upon the tissue type identified by the anatomy classifier 310. In some examples, the processor 300 may be configured to retrieve the selected TSP from memory 318 (e.g., local memory of the ultrasound scanner) and to cause the settings defined by the selected TSP (TSP settings 312) to be applied to the system, such as by coupling corresponding commands to controller(s) 301. In some examples, the processor 300 may be configured to alternatively or additionally couple the TSP settings 312 as inputs to the settings prediction model 320. Thus, in some examples, the settings prediction model 320 may be configured to output predicted settings 314 based further in part on the current settings of the system, which in this case would be the settings defined by a previously selected TSP. In some such examples, the setting prediction model 320 may be configured to receive an input vector having a dimension n+i, where n corresponds to the number of settings defined by the TSP and i corresponds to the number of additional input variables such as one or more user identification parameters (e.g., an alphanumeric user ID, biometric ID input, etc.) and one or more patient identification parameters (e.g., patient name, medical record ID, patient sex, age, weight, etc.), and to generate an output vector having a dimension n.

Figure 4:
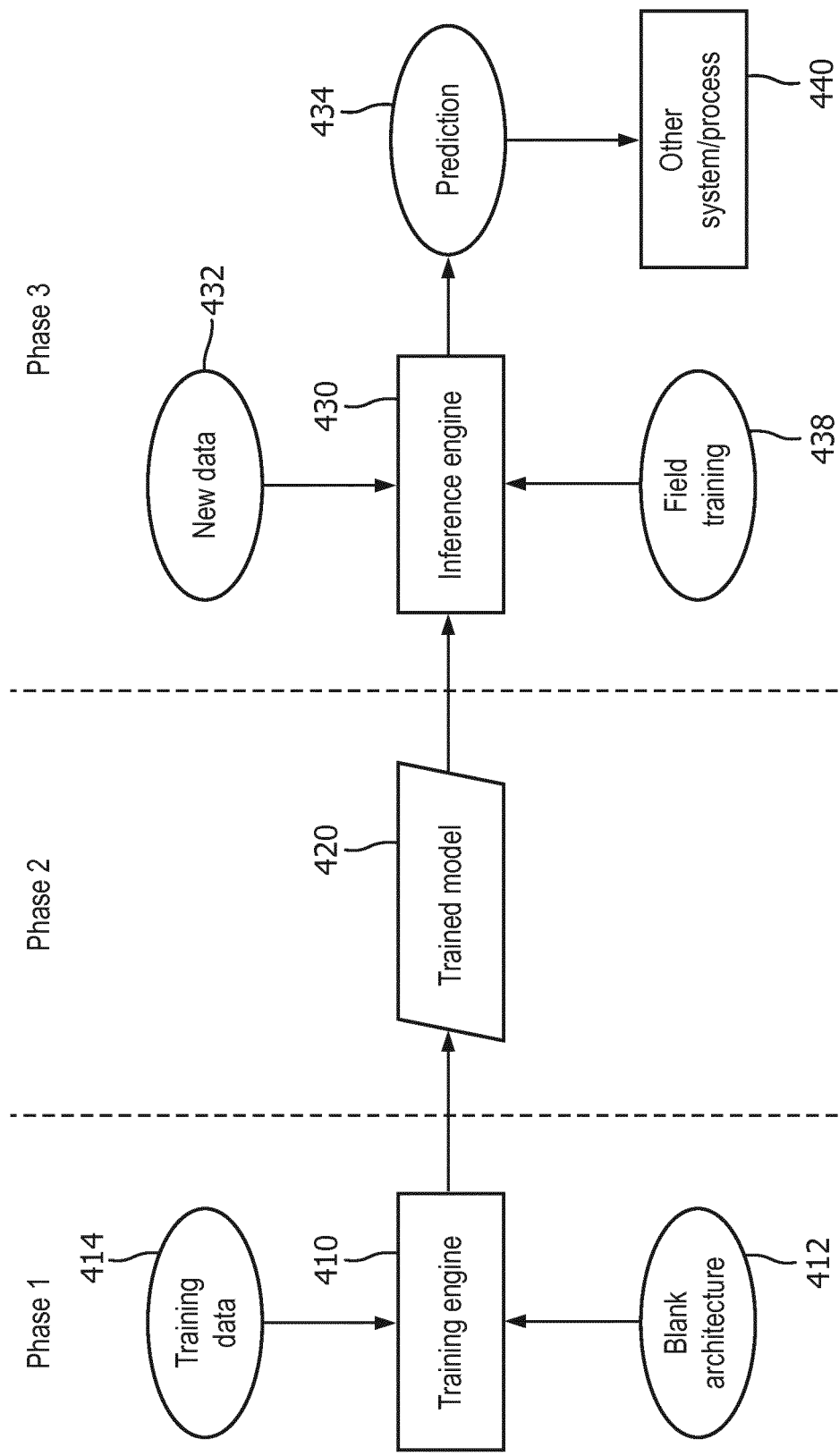
FIG. 4 shows a methodology for training and deploying an artificial neural network (or machine-learning model) in an ultrasound imaging system in accordance with the present disclosure.

FIG. 4 shows a block diagram of a process for training and deployment of a neural network in accordance with the principles of the present disclosure. The left hand side of FIG. 4, phase 1, illustrates the training of a neural network. Training may involve the selection of a starting network architecture 412 and the preparation of training data 414. The starting network architecture 412 may be a blank architecture (e.g., an architecture with defined layers and arrangement of nodes but without any previously trained weights) or a partially trained network, such as the inception networks, which may then be further tailored for classification of ultrasound images. The starting architecture 412 (e.g., blank weights) and training data 414 are provided to a training engine 410 for training the model. Upon sufficient number of iterations (e.g., when the model performs consistently within an acceptable error), the model 420 is said to be trained and ready for deployment, which is illustrated in the middle of FIG. 4, phase 2. The right hand side of FIG. 4, or phase 3, the trained model 420 is applied (via inference engine 430) for analysis of new data 432, which is data that has not been presented to the model during the initial training (in phase 1). For example, the new data 432 may include unknown images such as live ultrasound images acquired during a scan of a patient. The trained model 420 implemented via engine 430 is used to classify the unknown images in accordance with the training of the model 420 to output a prediction 434 (e.g., classification(s) of the type of tissue represented in the input image). The prediction 434 (e.g., type of biological tissue) may then be used by the system for subsequent processes 440 (e.g., as input to one or more other machine-learning models, and for effecting an action by the system such as the automated reconfiguration of the system's imaging parameters).

In the examples where the trained model 420 is a classification model, the starting architecture may be that of a convolutional neural network, or a deep convolutional neural network, which may be trained to perform image classification, image segmentation, image comparison, or any combinations thereof. With the increasing volume of stored medical image data (e.g., in PACS or in cloud storage), the availability of high-quality clinical images is increasing, which may be leveraged to train a neural network to learn the probability of a given image containing a given type of tissue. The training data 414 may include multiple (hundreds, often thousands or even more) annotated/labeled images, also referred to as training images. It will be understood that the training image need not include a full image produced by an imagining system (e.g., representative of the full field of view of the probe) but may include patches or portions of images of the labeled type of biological tissue.

Figure 5:
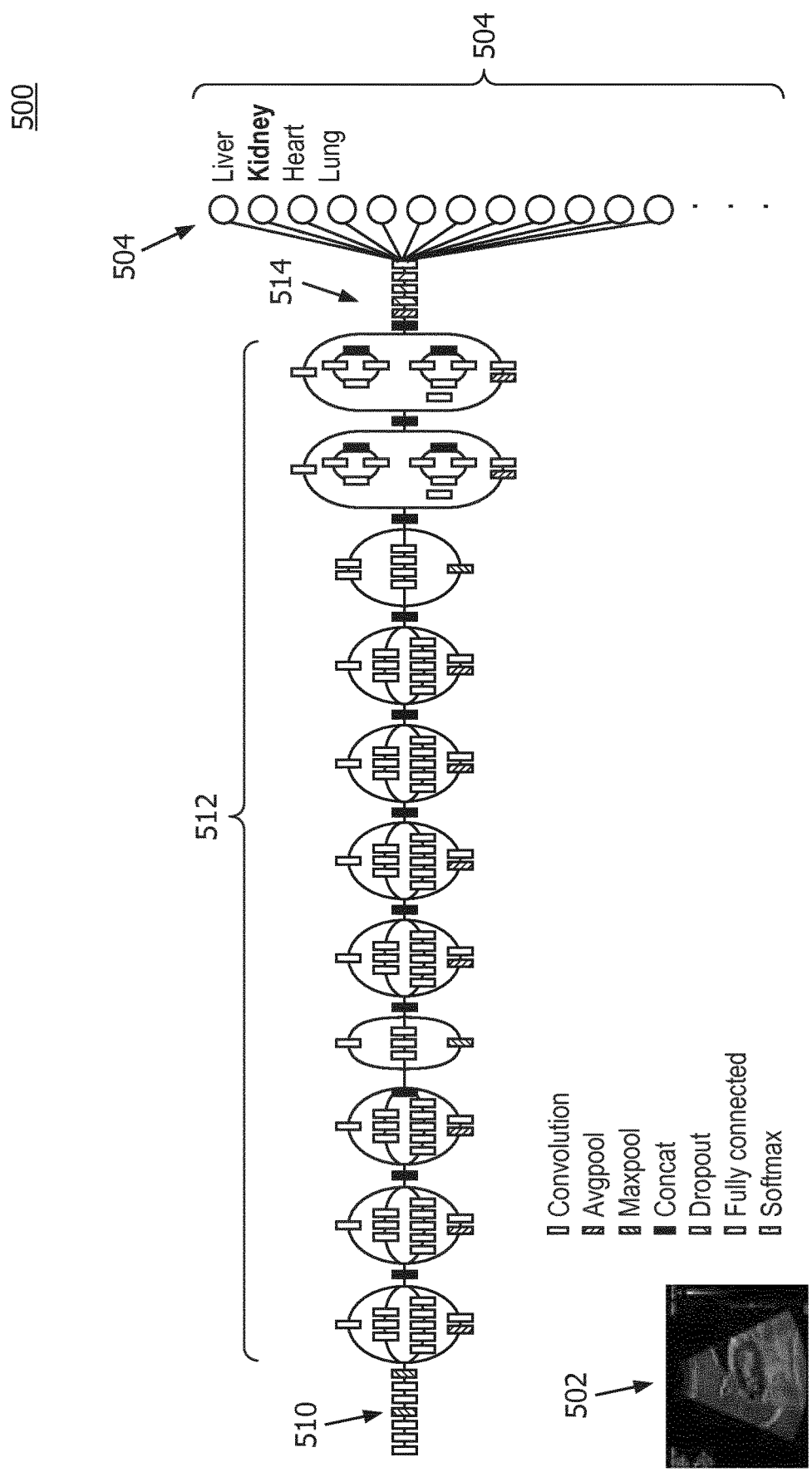
FIG. 5 shows an illustration of an example neural network architecture which may be used to implement an anatomy classification model in accordance with the present disclosure.

FIG. 5 shows an example architecture for a neural network 500 which may be trained to perform ultrasound image classification in accordance with the principles of the present disclosure. The neural network 500 may include any suitable number and arrangement of layers including an input layer 510, a plurality of intermediate or hidden layers 512 (e.g., convolution, normalization, pooling, fully connected, or other types of layers), and an output layer 514. The input layer 510 is configured to receive an input corresponding to an ultrasound image 502. The intermediate layers 512, for example in the case of a convolutional network, are configured to apply a plurality of filters to the input(s) to each successive layer starting with the input layer, to generate a stack of feature maps, which may then be provided to a fully connected output layer 512 configured to output a classification of the image into one of a plurality of possible categories 518 or the probabilities of the image falling in each of the possible categories. Thus in some examples the output layer 514 provides an output vector 504 having a dimension equal to the number of possible categories 518 (e.g., liver, kidney, heart, lung, breast, fetal, vascular, etc.). In some example, the network 500 may be configured to provide as output, only a single classification, e.g., corresponding to the classification with the highest probability.

Any suitable architecture, such as ResNet, AlexNet, VGGNet, GoogLeNet, or others, may be used as a starting architecture for the neural network 500. In some examples, the starting architecture (e.g., 412 in FIG. 4) may be a "blank slate" network which may be trained from scratch (i.e., without any preconfiguration of the weights). As described with reference to FIG. 4, this starting architecture and a training data set may be provided to a training engine to train the network for the specific task, in this case for classifying an ultrasound image into one of a plurality of possible tissue type categories or classifications. In some examples, the starting architecture may be a partially trained network, such as the Inception v3 network trained on the ImageNet dataset, may be used as a starting point and then supplementally trained or fine-tuned with a further training dataset including only ultrasound images, thereby reducing the overall training time for arriving at an appropriately trained model. Thus, the supplemental training of a previously trained network architecture, such as Inception v3, involves refining the weights of the network and the dense (fully connected) layers to provide a multi-label classifier configured to generate an output vector having a length equal to the number of distinct tissue types represented in the training dataset.

In some instances, depending on the particular architecture of the neural network 500, the ultrasound image which is retrieved from the live stream may need to be pre-processed before it can be coupled to the neural network (e.g., 500) for classification. For example, when a network of the Inception v3 architecture is used, the live ultrasound image may first be pre-processed (e.g., reproduced in triplicate) to provide a 3-channel input as required by the Inception v3 architecture. In some examples, the triplicate representation of the incoming image may include three different representations of the full dynamic range of the originally acquired image (e.g., high signal with low dynamic range image, low signal with low dynamic range image, and a compressed high dynamic range image with adaptive histogram equal to the full dynamic range or otherwise defined). In some examples, the ultrasound system may natively output a multi-channel (either color or grayscale) image in which case the pre-processing step may be omitted or a different pre-processing step may be performed. Thus, depending on the architecture deployed in the field (e.g., on the ultrasound system 200), the processor which communicates with the neural network may or may not require a pre-processing block, as described herein. As further described, the neural network 500 may include or be operatively connected to a post-processing block, for example for selecting one of the plurality of tissue type categories (e.g., the category associated with the highest probability value), which can then be provided as input to downstream processing blocks (e.g., to the setting prediction model 320 and/or the selector block 316 in FIG. 3). While an example network architecture is shown in FIG. 5, it will be understood that in other examples other suitable architectures may be used to implement the tissue type detection component of the process.

Figure 6:
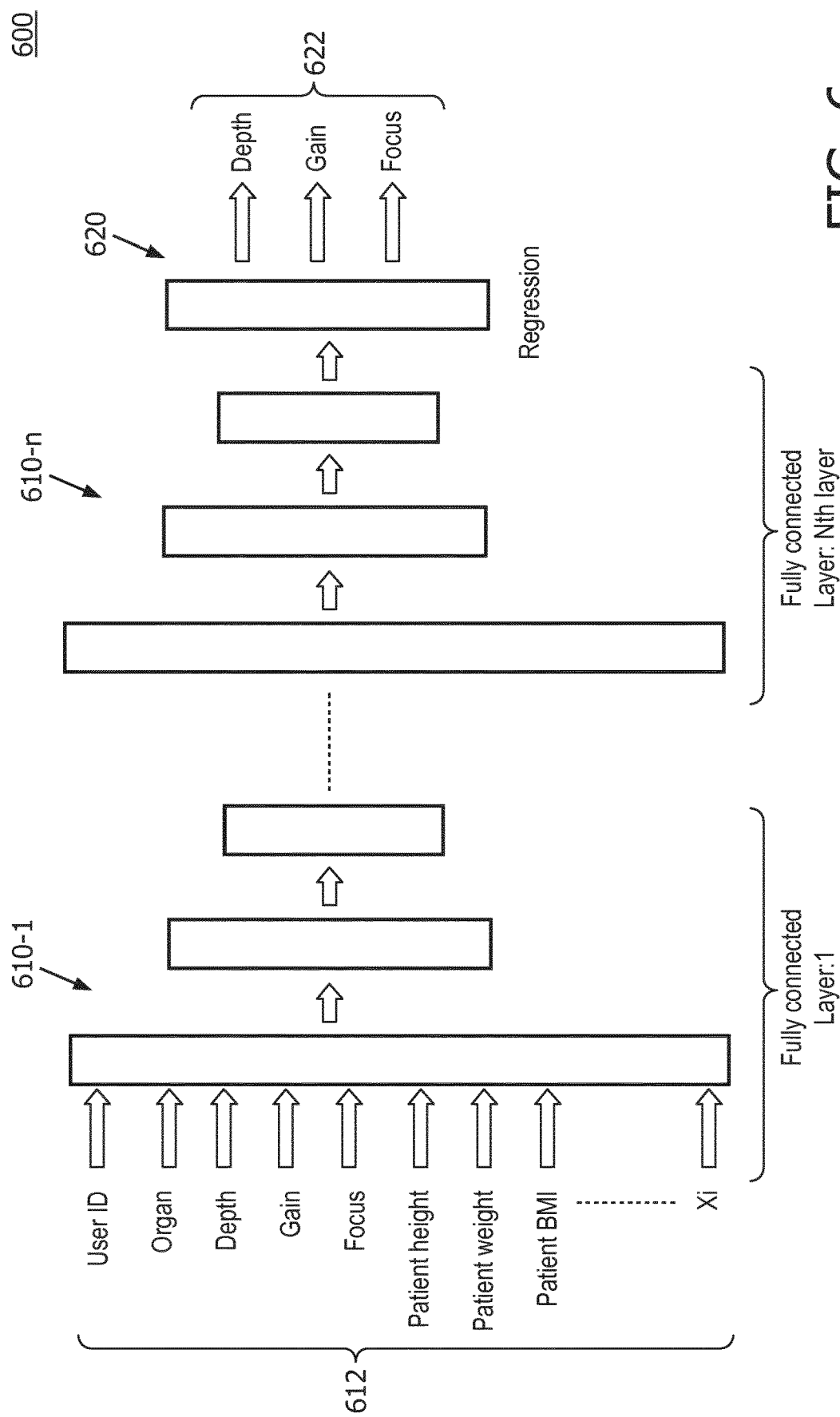
FIG. 6 shows an illustration of an example neural network architecture which may be used to implement a settings prediction model in accordance with the present disclosure.

FIG. 6 shows an example architecture for a neural network 600, which may be used to implement the settings prediction model 320. The neural network 600 may be configured to perform regression to arrive at the one or more predicted settings 622. For example, the neural network may include a plurality of fully connected layers (610-1 through 610-n), with the first fully connected layer functioning as the input layer configured to receive the input vector 612. The last (or output) layer of the network 600 is a regression layer 620 configured to generate the output vector 622, the individual elements of which define the predicted preferred settings for individual imaging parameters of the system.

Figures 8, 9:
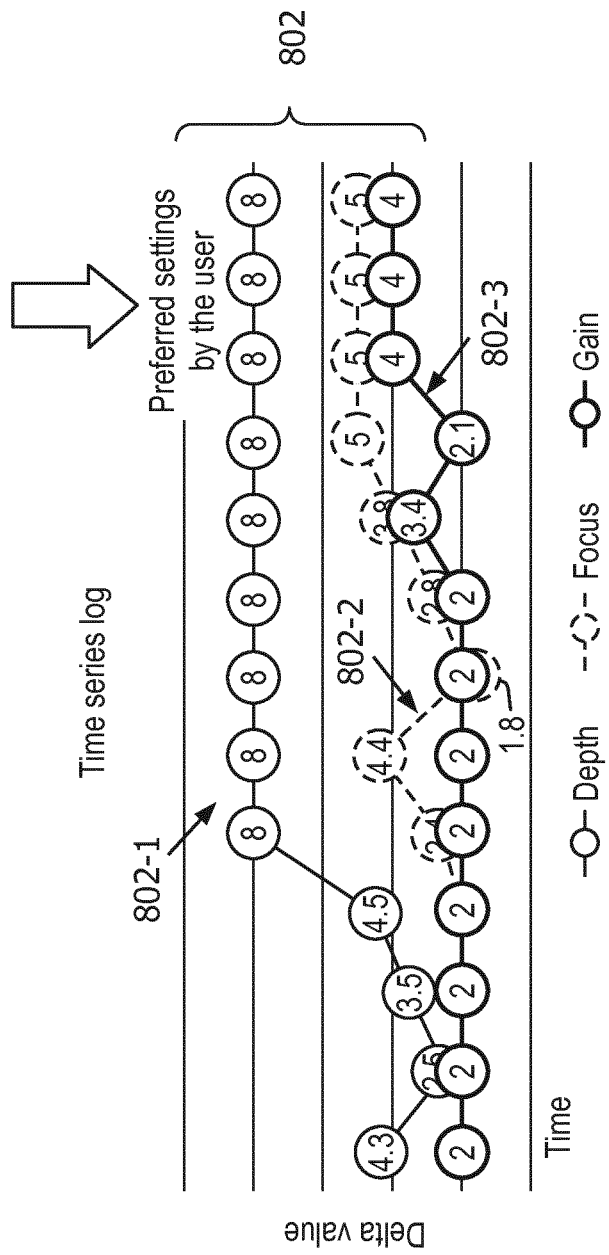
FIG. 8 shows plots of data extracted from the system logs in accordance with the present disclosure, more specifically showing the changes of three exemplary imaging parameters plotted as a function of time.
FIG. 9 shows a table of input parameters for use in training a setting prediction model in accordance with the present disclosure.

FIGS. 7-9 show aspects of training a machine-learning regression model (e.g., neural network 600) in accordance with the principles of the present disclosure. As described, the model may be trained using settings extracted from system log files. For example, FIG. 7A shows a portion of a system log 700, e.g., a utilization log generated by the ultrasound imaging system marketed under the brand name EPIQ by PHILIPS Ultrasound. The system log may track any adjustments made to the system such as to change imaging settings. The portion of the log 700 shows recorded information 710, 712 associated with a given user action, for example recording the type of user action (e.g., preset_activated 710 to indicate the selection of a preset) and the specific preset selected (e.g., Adult Echo 712). FIG. 7B shows a portion of another system log 720, e.g., a workflow log generated by the EPIQ system. The portion of log 720 shows the changes to the depth parameter, e.g., depth change events 722-1 and 722-2, with corresponding depth values 724-1 and 724-2 being set to 1 and 2, respectively.

To prepare the training data, a time series plots may be constructed from the data extracted from the system logs. For example, referring to FIG. 8, curves 802 may be generated for the individual imaging parameters of the system (e.g., depth, focus, gain, transmit/receive frequency, velocity range, dynamic ranged, etc.). Each of the curves 802 plots changes in the value of the corresponding parameter as a function of time. In the illustrated example, curve 802-1 shows a time series log of the depth setting, curve 802-2 shows the change over time of the focus setting, and curve 802-3 shows the change over time of the gain setting. The time series logs may be inspected, manually or with computer assistance, to identify the preferred settings for a particular combination of user and patient. For example, the curves may be inspected to identify a plateau in the curve, which may indicate that the user has arrived to a preferred setting. Additionally or alternatively, the curves may be inspected to identify a value of a given imaging parameter just prior to an image freeze, record and/or archive operation, thus this value may represent the preferred setting for the particular combination of user and patient. This data extraction process, which may be manual or at least partially computer-automated, may be performed for hundreds, thousands or more combinations of users and patients to compile the training data set. In some examples, the training data may be tabulated, for example as shown in table 902 of FIG. 9. Each row 904 (e.g., observation $X_1$ through $X_i$) therefore may correspond to a unique combination of input parameters to the settings prediction model which may be used to train the model. As noted, the table 902 may contain, hundreds, thousands or even more rows 904 of training data. In some examples, a portion of the tabulated data (e.g., up to 5%, up to 10%, or more) may be reserved as validation data and/or test data, to be used to validate and/or test the performance of the model prior to deployment. As described, patient information data may be alternatively or additionally extracted from other sources, such as from an electronic medical records (EMR) system and/or from annotations or metadata archived with the stored ultrasound images associated with the system logs. The training data, e.g., input parameter combinations of individual rows, may be provided to the model and the weights of the model may be iteratively updated (e.g., through backpropagation), and upon completion of training, the trained model may be tested to confirm performance of the model at or above the expected baseline accuracy level, at which point the model is deemed to have been appropriately trained (e.g., trained model 420) and ready for deployment (e.g., in the inference or prediction engine 430 such as the settings prediction engine 227 of system 200).

The examples herein may improve previously known ultrasound imaging systems in that they provide processor-implemented techniques for automated reconfiguration of the imaging system to acquire better quality images. In accordance with the examples herein, the system may automatically and dynamically reconfigure itself (e.g., apply better suited imaging parameters) responsive to the operator scanning a different area of the subject. This automated reconfiguration is achieved by one or more background processes which analyze the image data to identify the type of tissue that is being imaged, automatically select and apply an appropriate TSP for the type of tissue, and further automatically adjusting or adapting the settings defined by the selected TSP to settings that the systems determines to be preferred for the specific user and/or patient being imaged.

Although examples of producing medical images from sparsely sampled data are described herein with reference to ultrasound image data, it will be understood that the examples herein are equally applicable to training a neural network to produce images from a sparse dataset of any imaging modality, such as magnetic resonance imaging (MRI), computed tomography (CT), positron emission tomography (PET), and virtually any other imaging modality.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system with automated setting of imaging parameters during live imaging, the system comprising:
   a probe configured to transmit ultrasound toward a subject for generating ultrasound images of biological tissue of the subject;
   a processor configured to generate and to cause the ultrasound imaging system to display, in real-time, a live stream of ultrasound images of the biological tissue in accordance with a plurality of imaging parameters of the ultrasound system, wherein the processor is further configured to:
   receive, in real-time, an ultrasound image from the live stream of ultrasound images;
   receive an identification of a type of the biological tissue in the ultrasound image;
   receive subject identification information, user identification information, or a combination thereof;
   identify the subject as a recurring subject based at least in part on the subject identification information;
   based on the type of the biological tissue and the subject identification information, generate at least one predicted setting for the recurring subject for at least one of the plurality of imaging parameters; and
   apply the at least one predicted setting to the respective imaging parameter for subsequent live imaging of the recurring subject,
   wherein the processor is configured to generate the at least one predicted setting using an artificial neural network model, and
   wherein the artificial neural network model is a model trained using historical data extracted from system logs from multiple prior scans performed by a same user or of the recurring subject.

2. The system of claim 1, wherein the artificial neural network model is a machine-learning regression model.

3. The system of claim 2, wherein regression model is trained using data extracted from system logs from multiple ultrasound imaging systems.

4. The system of claim 1, wherein the processor is configured to generate the at least one predicted setting further based on a current setting for the at least one of the plurality of imaging parameters.

5. The system of claim 4, wherein the processor is configured to couple to a deep learning model a set of input parameters including a tissue type identification, a plurality of current settings for imaging parameters of the system including a current depth setting, a current gain setting, and a current focus setting, and at least one user identification input and at least one subject identification input.

6. The system of claim 1, wherein, to generate the at least one predicted setting, the processor is configured to execute a trained neural network model comprising a plurality of layers including a first input layer configured to receive an input of size n+i and an output layer configured to generate an output of size n, and wherein n is equal to a number of the settings defined by the selected preset and i is equal to a number of additional input variables.

7. The system of claim 6, wherein the trained neural network model comprises a plurality of intermediate fully connected layers, and wherein the output layer is a fully connected regression layer.

8. The system of claim 1, wherein the processor is further configured to automatically determine the type of the biological tissue in the ultrasound image upon receiving the ultrasound image from the live stream of ultrasound images.

9. The system of claim 8, wherein the processor is configured to use a machine-learning classification model to identify the type of the biological tissue.

10. The system of claim 9, wherein the processor is configured to use a machine-learning classification model having a convolutional neural network architecture for identifying the type of the biological tissue.

11. The system of claim 1, further comprising memory storing a plurality of presets, each defining one or more settings for at least one of the plurality of imaging parameters of the ultrasound imaging system, and wherein the processor is further configured to:
   select one of the plurality of stored presets based on the type of the biological tissue; and
   provide the one or more settings of the selected preset as inputs to the artificial neural network.

12. The system of claim 11, wherein the processor is further configured to automatically adjusting corresponding one or more of the plurality of imaging parameters of the ultrasound system to settings defined by the selected preset prior to or while generating the at least one predicted setting.

13. A method of live ultrasound imaging of biological tissue, the method comprising:
   receiving, in real-time, by a processor of an ultrasound system, an ultrasound image from a live stream of ultrasound images of a subject, wherein ultrasound images in the live stream, including the ultrasound image, are generated in accordance with current settings of a plurality of imaging parameters of the ultrasound system;
   receiving an identification of a type of the biological tissue in the ultrasound image;
   receiving subject identification information, user identification information, or a combination thereof;
   identifying the subject as a recurring subject based at least in part on the subject identification information;
   based on the type of the biological tissue and the subject identification information, generating a predicted setting for the recurring subject for at least one of the plurality of imaging parameters; and
   automatically adjusting the current setting of the at least one of the of the plurality of imaging parameters in accordance with the predicted setting for subsequent live imaging of the recurring subject,
   wherein the generating the predicted setting is based on use of an artificial neural network model, and
   wherein the artificial neural network model is a model trained using historical data extracted from system logs from multiple prior scans performed by a same user or of the recurring subject.

14. The method of claim 13, wherein the generating includes coupling the type of the biological tissue and the subject identification information to an artificial neural network comprising an input layer configured to receive a multi-dimensional input vector, a plurality of intermediate layers, and an output regression layer configured to output a multi-dimensional output vector having a smaller dimension than the input vector.

15. The method of claim 14, wherein the output layer and the intermediate layers are fully connected layers.

16. The method of claim 14, further comprising selecting one of a plurality of presets, each defining one or more settings for at least one of the plurality of imaging parameters of the ultrasound imaging system, from a memory of the ultrasound system, and providing the one or more settings of the selected preset as input to the artificial neural network.

17. The method of claim 16, further comprising automatically adjusting one or more of the plurality of imaging parameters of the ultrasound system to settings defined by the selected preset prior to or while generating the at least one predicted setting.

18. The method of claim 13, further comprising determining, by the processor, the type of the biological tissue in the ultrasound image responsive to receiving the ultrasound image from the live stream of ultrasound images.

19. The method of claim 18, wherein the determining includes coupling the ultrasound image from the live stream to another artificial neural network trained to perform organ classification on an input ultrasound image.

20. A non-transitory computer-readable medium comprising executable instructions, which when executed cause a processor of a medical imaging system to perform the method of claim 12.

21. A method of developing and deploying a system for live ultrasound imaging according to claim 13, the method further comprising training a neural network model to generate the predicted setting and storing the trained neural network model as processor-executable instructions in a computer-readable medium of the system, wherein the training comprises:
  extracting a plurality of user preferred settings from system logs of at least one ultrasound imaging system;
  generating sets of training data, each set including at least one user preferred setting from the plurality of user preferred settings and a user identification parameter associated with the at least one user preferred setting;
  conducting training of the neural network model using a first subset of the training data; and
  validating performance of the trained neural network model using a second subset of the training data.

22. The system of claim 1, wherein the at least one predicted setting for at least one of the plurality of imaging parameters is generated based further on the user identification information.

23. The method of claim 13, wherein generating the predicted setting for at least one of the plurality of imaging parameters is further based on the user identification information.

* * * * *